(12) United States Patent
Taira et al.

(10) Patent No.: US 6,740,750 B1
(45) Date of Patent: May 25, 2004

(54) EXPRESSION SYSTEMS FOR FUNCTIONAL NUCLEIC ACID EXPRESSION

(75) Inventors: Kazunari Taira, Ibaraki (JP); Jun Ohkawa, Ibaraki (JP); Shiori Koseki, Yamagata (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 09/763,590

(22) PCT Filed: Aug. 31, 1999

(86) PCT No.: PCT/JP99/04718

§ 371 (c)(1),
(2), (4) Date: Feb. 26, 2001

(87) PCT Pub. No.: WO00/12686

PCT Pub. Date: Mar. 9, 2000

(30) Foreign Application Priority Data

Aug. 31, 1998 (JP) ............................................. 10-244755

(51) Int. Cl.[7] ...................... C07H 21/02; C07H 21/04; C12P 19/34; C12Q 1/68; C12N 15/85
(52) U.S. Cl. .................... 536/24.5; 435/6; 435/91.1; 435/91.3; 435/325; 435/375
(58) Field of Search .................... 435/6, 91.1, 91.3, 435/325, 375; 536/23.2, 24.3, 24.31, 24.33, 24.5; 514/44

(56) References Cited

U.S. PATENT DOCUMENTS 5,670,361 A   9/1997   Wong-Staal et al.

FOREIGN PATENT DOCUMENTS

WO   WO 94/00012   1/1994
WO   WO 96/22368   7/1996

OTHER PUBLICATIONS

Agrawal et al., Molecular Medicine Today, Vol 6, p 72–81, Feb. 2000.*
Branch, A. D., TIBS 23, Feb. 1998, p45–50.*
Green et al., J. Am Coll. Surg., vol. 191. No. 1. Jul. 2000, p 93–105.*
Jen et al., Stem Cells 2000. Vol. 18, p 307–319.*
Verma et al. Nature, vol. 389. Sep. 18, 1997, pp. 239–242.*
Anderson, W. F. Nature, vol. 392, Apr. 30, 1998, pp. 25–30.*
Domi et al., "Transcripts Containing A Small Anti–HIV Hammerhead Ribozyme That Are Active In The Cel Cytoplasm But Inactive In Vitro As Free mRNAs," *Biochimie*, 78: 654–662, 1996.
European Search Report for Application No. 99940588.9, mailed Oct. 21, 2002.

(List continued on next page.)

*Primary Examiner*—Karen A. Lacourciere
(74) *Attorney, Agent, or Firm*—Finnegan, Henderson, Farabow, Garrett & Dunner, L.L.P.

(57) ABSTRACT

A ribozyme comprising the following base sequence (I) or (II):

base sequence (I)(SEQ ID No. 1):
5'-ACCGUUGGUUUCCGUAGUGUAGU GGUUAUCACGUUCGCCUAACACGC- GAAAGGUCCCCGGUUCGAAACCGGGCACU ACAAACACAACACUGAUGAGGAC- CGAAAGGUCCGAAACGGGCACGUCGGAAACG GUUUU[[U]]-3' base sequence (II)(SEQ ID No. 2):
5'-ACCGUUGGUUUCCGUAGUGUAGUGG UUAUCACGUUCGCCUAACACGCGAAAG- GUCCCCGGUUCGAAACCGGGCACUACAAA CCAACACACAACACUGAUGAGGAC- CGAAAGGUCCGAAACGGGCACGUCG- GAAACGG UUUU[[U]]-3'.

9 Claims, 7 Drawing Sheets

OTHER PUBLICATIONS

Homann et al., "Incorporation Of The Catalytic Domain Of A Hammerhead Ribozyme Into Antisense RNA Enhances Its Inhibitory Effect On The Replication Of Human Immunodeficiency Virus Type 1 ," *Nucleic Acids Research*, 21: 2809–2814, 1993.

Rossi et al., "Ribozymes as ANti–HIV–1 Therapeutic Agents: Principles, Applications, And Problems," *AIDS Research and Human Retroviruses*, 8: 183–189, 1992.

Sakamoto et al., "Intracellular Cleavage Of Hepatitis C Virus RNA And Inhibition of Viral Protein Translation By Hammerhead Ribozymes," *J. Clin. Invest.*, 98: 2720–2728, 1996.

Sun et al., "Ribozyme–Mediated Suppression of Moloney Murine Leukemia Virus And Human Immunodeficiency Virus Type I Replication In Permissive Cell Lines," *Proc. Natl. Acad. Sci. USA*, 91: 9715–9719, 1994.

Weerasinghe et al., "Resistance To Human Immunodeficiency Virus Type I (HIV–1) Infection In Human CD4+ Lymphocyte–Derived Cell Lines Conferred By Using Retroviral Vectors Expressing An HIV–1 RNA–Specific Ribozyme," *J. Virol.*, 65: 5531–5534, 1991.

Adachi, et al, "Production of Acquired Immunodeficiency Syndrome–Associated Retrovirus in Human, and Nonhuman Cells Transfected with an Infectious Molecular Clone," *Journal of Virology*, 59(1): 284–291 (1986).

Adeniyi–Jones, et al, "Generation of Long Read–Through Transcripts in vivo and in vitro by Deletion of 3' Termination and Processing Sequences in the Human tRNA,$^{mef}$ Gene," *Nucleic Acids Res.*, 12: 1101–1115 (1984).

Arnold, et al, "The Human tRNA$^{val}$ Gene Family: Organization, Nucleotide Sequences and Homologous Transcription of Three Single–Copy Genes," *Gene*, 44: 287–297 (1986).

Arts, et al., "Identification of a Nuclear Export Receptor for tRNA," *Curr. Biol.*, 8: 305–314 (1998).

Bertrand, et al. "Can Hammerhead Ribozymes be Efficient Tools to Inactive Gene Function?," *Nucleic Acids Res.*, 22:293–300 (1994).

Bertrand, et al., "Anti–HIV Therapeutic Hammerhead Ribozymes: Targeting Strategies and Optimization of Intracellular Function," in *Nucleic Acids Molecular Biology: Catalytic RNA* 310–313 (Eckstein and Lilley eds., 1996).

Bertrand, et al., "The Expression Cassette Determines the Functional Activity of Ribozymes in Mammalian Cells by Controlling their Intracellular Localization," *RNA*, 3: 75–88 (1997).

Boelens, et al., "Nuclear Retention of RNA as a Mechansim for Localization," *RNA*, 1(3): 273–283 (1995).

Cotten, et al, "Ribozyme Mediated Destruction of RNA in vivo," *The EMBO Journal*, 8(12):3861–3866 (1989).

Dahm, et al., "Role of Divalent Metal Ions in the Hammerhead RNA Cleavage Reaction," *Biochemistry*, 30(39): 9464–9469 (1991).

Dahm, et al., "Evidence for the Role of Solvated Metal Hydroxide in the Hammerhead Cleavage Mechanism," *Biochemistry*, 32 (48): 13040–13045 (1993).

Dropulić, et al., "Functional Characterization of a U5 Ribozyme: Intracellular Suppression of Human Immunodeficiency Virus Type 1 Expression," *Journal of Virology*, 66(3): 1432–1441 (1992).

Ferbeyre, et al, "Cell Cycle Arrest Promotes *trans*–Hammerhead Ribozyme Action in Yeast," *The Journal of Biological Chemistry*, 271(32): 19318–19323 (1996).

Fujita, et al, "Discrimination of a Single Base Change in a Ribozyme Using the Gene for Dihydrofolate Reductase as a Selective Marker in *Escherichia coli*," *Proceedings of the National Academy of Sciences*, 94(2): 391–196 (1997).

Gebhard, et al., "Use of a Nonviral Vector to Express a Chimeric tRNA–Ribozyme Against Lymphocytic Choriomeningitis Virus: Cytoplasmic Accumulation of a Catalytically Competent Transcript but Minimal Antiviral Effect," *Antisense & Nucleic Acid Drug Development*, 7(1):3–11 (1997).

Good, et al., "Expression of Small, Therapeutic RNAs in Human Cell Nuclei," *Gene Therapy*, 4(1): 45–54 (1997).

Guerrier–Takada, et al., "The RNA Moiety of Ribonuclease P is the Catalytic Subunit of the Enzyme," *Cell*, 35(3): 849–857 (1983).

Hamblet, et al., "Mitochondrial DNA Deletion Analysis: A Comparison of PCR Quantitative Methods," *Biochemical and Biophysical Research Communications*, 207(2): 839–847 (1995).

Haseloff et al., "Simple RNA Enzymes with New and Highly Specific Endoribonuclease Activities," *Nature*, 334(6183): 585–591 (1988).

Huang, et al., "Role of Polyadenylation in Nucleocytoplasmic Transport of mRNA," *Molecular and Cellular Biology*, 16(4): 1534–1542 (1996).

Inokuchi, et al., "A Hammerhead Ribozyme Inhibits the Proliferation of an RNA Coliphage SP in *Escherichia coli*," *The Journal of Biological Chemistry*, 269(15): 11361–11366 (1994).

Ilves, et al., "Retroviral Vectors Designed for Targeted Expression of RNA Polymerase III–Driven Transcpits: A Comparative Study," *Gene*, 171(2): 203–208 (1996).

Jennings, et al., "Inhibition of SV40 Replicon Function by Engineered Antisense RNA Transcribed by RNA Polymerase III," *The EMBO Journal*, 6(10): 3043–3047 (1987).

Kawasaki, et al., "Selection of the Best Target Site for Ribozyme–Mediated Cleavage Within a Fusion Gene for Adenovirus E1A–Associated 300 kDa Protein (p300) and Luciferase," *Nucleic Acids Research*, 24(15): 3010–1016 (1996).

Kawasaki, et al., "Distinct Roles of the Co–Activators p300 and CBP in Retinoic–Acid–Induced F9–Cell Differentiation," *Nature*, 393: 284–289 (1998).

Kruger, et al., "Self–Splicing RNA: Autoexcision and Autocyclization of the Ribosomal RNA Intervening Sequence of Tetrahymena," *Cell*,31(1): 147–157 (1982).

Lott, et al., "A Two–Metal Ion Mechanism Operates in the Hammerhead Ribozyme–Mediated Cleavage of an RNA Substrate." *Proceedings of the National Academy of Sciences.* 95(2): 542–547 (1998).

Ohkawa, et al., "Importance of Independence in Ribozyme Reactions: Kinetic Behavior of Trimmed and of Simply Connected Multiple Ribozymes with Potential Activity Against Human Immunodeficiency Virus," *Proceedings of the National Academy of Sciences*, 90(23): 11302–11306 (1993).

Ojwang, et al., "Inhibition of Human Immunodeficiency Virus Type 1 Expression by a Hairpin Ribozyme," *Proceedings of the National Academy of Sciences*, 89(22): 10802–10806 (1992).

Ozawa, et al., "Quantitative Determination of Deleted Mitochondrial DNA Relative to Normal DNA in Parkinsonian Striatum by a Kinetic PCR Analysis," *Biochemical and Biophysical Research Communications*, 172(2): 483–489 (1990).

Perriman, et al., "Effective Ribozyme Delivery in Plant Cells," *Proceedings of the National Academy of Sciences*, 92(13): 6175–6179 (1995).

Pontius, et al., "Observations on Catalysis by Hammerhead Ribozymes are Consistent with a Two–Divalent–Metal–Ion Mechanism," *Proceedings of the National Academy of Sciences*, 94(6): 2290–2294 (1997).

Prislei, et al., "Use of Adenoviral VAI Small RNA as a Carrier for Cytoplasmic Delivery of Ribozymes," *RNA*, 3(6): 677–687 (1997).

Rossi, et al., "RNA Enzymes (Ribozymes) as Antiviral Therapeutic Agents," *Trends in Biotechnology*, 8: 179–183 (1990).

Rossi, "Controlled, Targeted, Intracellular Expression of Ribozymes: Progress and Problems," *Trends in biotechnology*, 13:301–306 (1995).

Sarver, et al., "Ribozymes as Potential Anti–HIV–1 Theraputic Agents," *Science*, 247: 1222–1225 (1990).

Shimada, et al., "Targeted and Highly Efficient Gene Transfer into CD4 Cells by a Recombinant Human Immunodeficiency Virus Retroviral Vector," *Journal of Clinical Investigations*, 88: 1043–1047 (1991).

Smith, et al., "Transfer RNA in Retriculocyte Maturation," *Biochemica et Biophsica Acta*, 655(2): 195–198 (1981).

Sullenger, et al., "Expression of Chimeric tRNA–Driven Antisense Transcripts Renders NIH 3T3 Cells Highly Resistant to Moloney Murine Leukemia Virus Replication," *Molecular and Cellular Biology*, 10(12): 6512–6523 (1990).

Sullenger, et al., "Tethering Ribozymes to a Retroviral Packaging Signal for Destruction of Viral RNA," *Science*, 262: 1566–1569 (1993).

Taira, et al., "Construction of a Novel RNA–Transcript-Trimming Plasmid Which can be Used both in vitro in Place of Run–Off and (G)–Free Transcriptions and in vivo as Multi–Sequences Transcription Vectors," *Nucleic Acids Research*, 19(19): 5152–5130 (1991).

Thomas, et al., "Site–Directed Mutagenesis by Gene Targeting in Mouse Embryo–Derived Stem Cells," *Cell*, 51(3): 503–512 (1987).

Thompson, et al., "Improved Accumulation and Activity of Ribozymes Expressed from a tRNA–Based RNA Polymerase III Promoter," *Nucleic Acids Research*, 3(12): 2259–2268 (1995).

Tobian et al., "tRNA Nuclear Transport: Defining the Critical Regions of Human tRNA,$^{met}$ by Point Mutagenesis," *Cell*, 43: 415–422 (1985).

Uhlenbeck, "A Small Catalytic Oligoribonucleotide," *Nature*, 328 (6131): 596–600 (1987).

Yamada, et al., "Activity and Cleavage Site Specificity of an Anti–HIV–1 Hairpin Ribozyme in Human T Cells," *Virology*, 205(1): 121–126 (1994).

Yamada, et al., "Intracellular Immunization of Human T Cells with a Hairpin Ribozyme Against Human Immunodeficiency Virus Type 1," *Gene Therapy*, 1(1):38–45 (1994).

Yates, et al., "A cis–Acting Element from the Epstein–Barr Viral Genome that Permits Stable Replication of Recombinant Plasmids in Latently Infected Cells," *Proceedings of the Natural Academy of Sciences*, 81(12):3806–3810 (1984).

Yu, et al., "A Hairpin Ribozyme Inhibits Expression of Diverse Strains of Human Immunodeficiency Virus Type 1," *Proceedings of the National Academy of Science*, 90(13): 6340–6344 (1993).

Zhao, et al., "Generating Loss–of–Function Phenotypes of the fushi tarazu Gene with a Targeted Ribozyme in Drosophila," *Nature*, 365(6445): 448–451 (1993).

Zhou, et al., "Ribozyme Mechanism Revisited: Evidence Against Direct Coordination of a $Mg^{2+}$Ion with the pro–R Oxygen of the Scissile Phosphate in the Transition State of a Hammerhead Ribozyme–Catalyzed Reaction," *Journal of the American Chemical Society*, 118(37): 8969–8970 (1996).

Zhou, et al., "Explanation by the Double–Metal–Ion Mechanism of Catalysis for the Differential Metal ion Effects on the Cleavage Rates of 5'–oxy and 5'–thio Substrates by a Hammerhead Ribozyme," *Proceedings of the National Academy of Sciences*, 94(26): 14343–14348 (1997).

Zhou, et al., "The Hydrolysis of RNA: From Theoretical Calculations to the Hammerhead Ribozyme–Mediated Cleavage of RNA," *Chemical Reviews*, 98(3): 991–1026 (1998).

* cited by examiner

A  substrate RNA binding with the substrate
(secondary prediction map)

B

A

B

EXPRESSION SYSTEMS FOR FUNCTIONAL NUCLEIC ACID EXPRESSION

TECHNICAL FIELD

The present invention relates to ribozymes and their expression systems.

BACKGROUND ART

A hammerhead ribozyme is one of the smallest catalytic RNA Molecules (Kruger et al., 1982; Guerrier-Takada et al., 1983). Because of its small size and potential as an antiviral agent, numerous mechanistic studies (Dahm and Uhlenbech, 1991, Dahm et al., 1993; Eckstein and Lilley, 1996; Pontius et al., 1997; Lott et al., 1998; Zhou et al., 1996, 1997; Zhou and Taira, 1998) and studies directed towards application in vivo have been performed (Erickson and Izant, 1992; Murray, 1992; Rossi, 1995; Eckstein and Lilley, 1996; Prislei et al., 1997; Turner, 1997; Scanlon, 1997). Many successful experiments, aimed at the use of ribozymes for suppression of gene expression in different organisms, have been reported (Sarver et al., 1990; Dropulic et al., 1992; Ojwang et al, 1992; Yu et al, 1993; Zhao and Pick, 1993; Inokuchi et al, 1994; Yamada et al., 1994; Ferbeyre et al, 1996; Fujita et al, 1997; Kawasaki et al, 1998). However, the efficacy of ribozymes in vitro is not necessarily correlated with functional activity in vivo. Some of the reasons for this ineffectiveness in vivo are as follows. i) Cellular proteins may inhibit the binding of the ribozyme to its target RNA or may disrupt the active conformation of the ribozyme. ii) The intracellular concentration of metal ions essential for ribozyme-mediated cleavage might not be sufficient for functional activity. iii) Ribozymes are easily attacked by RNases. However, we are now starting to understand the parameters that determine ribozyme activity in vivo (Bertrand and Rossi, 1996; Bertrand et al., 1997; Gebhard et al., 1997). Studies in vivo have suggested that the following factors are important for the effective ribozyme-mediated inactivation of genes: a high level of ribozyme expression (Yu et al., 1993); the intracellular stability of the ribozyme (Rossi and Sarver, 1990; Eckstein and Lilley, 1996); co-localization of the ribozyme and its target RNA in the same cellular compartment (Sullenger and Cech, 1993; Bertrand et al., 1997); and the cleavage activity of the transcribed ribozyme (Thompson et al., 1995). Recently, it was shown that these various features depend on the expression system that is used (Bertrand et al., 1997).

The RNA polymerase II (pol II) system, which is employed for transcription of mRNAs, and the polymerase III (pol III) system, employed for transcription of small RNAs, such as tRNA and snRNA, have been used as ribozyme expression systems (Turner, 1997). Transcripts driven by the pol II promoter have extra sequences at the 3' and 5' ends (for example, an untranslated region, a cap structure, and a polyA tail), in addition to the coding region. These extra sequences are essential for stability in vivo and functional recognition as mRNA. A transcript containing a ribozyme sequence driven by the pol II promoter includes all those sequences, unless such sequences are trimmed after transcription (Taira et al., 1991; Ohkawa et al., 1993). As a result, in some case, the site by which the ribozyme recognizes its target may be masked, for example, by a part of the coding sequence. By contrast, the pol III system is suitable for expression of short RNAs and only very short extra sequences are generated. In addition, expression is at least one order of magnitude higher than that obtained with the pol II system (Cotten and Birnstiel, 1989). Thus, it was suggested that the pol III system might be very useful for expression of ribozymes (Yu et al., 1993; Perriman et al., 1995). However, in many cases, the expected effects of ribozymes could not be achieved in spite of the apparently desirable features of the pol III system (Ilves et al., 1996; Bertrand et al., 1997).

DISCLOSURE OF THE INVENTION

In order to investigate the parameters that determine ribozyme activity in vivo, we designed three types of ribozyme with an identical ribozyme sequence, driven by tRNA$^{Val}$ promoter which is a pol III promoter, and demonstrated that the entire structure of the transcript (ribozyme to which the sequence of tRNA$^{Val}$ is added (hereinafter termed "tRNA$^{Val}$-ribozyme")) determined not only cleavage activity but also the intracellular half-life of the ribozyme. All the chimeric tRNA$^{Val}$-ribozymes that were transcribed in the cell nucleus were exported to the cytoplasm. Thus, the ribozymes and their target were present within the same cellular compartment. Under these conditions, we found that the intracellular half-life and the steady-state level of each tRNA$^{Val}$-ribozyme were the major determinants of functional activity in vivo. Moreover, we demonstrated that cells that expressed a specifically designed ribozyme with the longest half-life in vivo were almost completely resistant to a challenge by HIV-1. Further, by establishing a small bulge structure ("bulge" refers to, in the case where RNA adopts a hairpin structure, a portion where there is a protruding single-stranded structure of unmatched base pairs) at the amino-acyl stem portion of the tRNA$^{Val}$ structure, avoidance of recognition from the mature enzyme can be achieved and as a result, any RNA sequence comprising a ribozyme sequence connected to the 3' end can be made to exist intracellularly in a form where it is connected to tRNA$^{Val}$. Any RNA comprising a ribozyme sequence connected to the 3' end of the tRNA$^{Val}$ structure of the present invention, due to the properties of the tRNA structure, is transported stably and efficiently to the cytoplasm. This is of particular importance for the intracellular function of the ribozyme.

A summary of the present invention is presented as follows:

1. A ribozyme comprising a nucleotide sequence having the following base sequence (I) or (II):

base sequence (II) (SEQ ID NO. 1):
    5'-ACCGUUGGUUUCCGUAGUGU AGUGG-UUAUCACGUUCGCCUAACACGCGAAAG-GUCCCCGGUUCGAAACCGGGCAC UACAAA-CACMCACUGAUGAGGACCGAAAGGUCCGA AACGGGCACGUCGGAAACGG UUUU[[U]]-3' base sequence (II)(SEQ ID NO. 2):
    5'-ACCGUUGGUUUCCGUAGUGUAGUG GUUAUCACGUUCGCCUAACACGCGAAAG-GUCCCCGGUUCGAAACCGGGCACUACM ACC-MCACACMCACUGAUGAGGACCGAAAG-GUCCGAAACGGGCACGUCGGAAACG GUUUU [[U]]-3'.

2. An expression vector comprising DNA encoding the ribozyme according to 1 above.

3. A method of producing the ribozyme according to 1 above comprising transcribing to RNA with expression vector DNA as a template, wherein said expression vector DNA comprises DNA encoding the ribozyme according to 1 above.

4. A pharmaceutical composition comprising the ribozyme according to 1 above or the expression vector according to 2 above, as an effective ingredient.

5. The pharmaceutical composition according to 4 above for the prevention and/or treatment of acquired immune deficiency syndrome.
6. A method of specifically cleaving a target RNA using the ribozyme according to 1 above.
7. The method of 6 above wherein the target RNA is HIV-1 RNA.
8. An RNA variant (mature tRNA$^{Val}$) adopting the following secondary structure (I), wherein said RNA variant comprises a bulge structure introduced in the region in which hydrogen bonds form between nucleotides 8 to 14 and nucleotides 73 to 79.

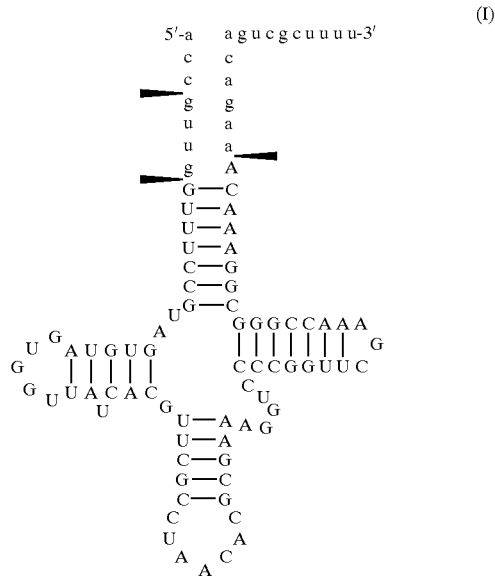

9. The RNA variant of 8 above wherein a bulge structure is introduced by substituting all or part of the sequence of the region corresponding to nucleotides 73 to 79 within a nucleotide sequence of an RNA adopting secondary structure (I).
10. The RNA variant according to 8 above consisting of the sequence of a region corresponding to nucleotides 1–80 within a nucleotide sequence represented by SEQ ID NO: 1.
11. The RNA variant according to 8 above consisting of the sequence of a region corresponding to nucleotides 1–86 within a nucleotide sequence represented by SEQ ID NO: 2.
12. An RNA comprising the RNA variant of 8 above and a selected RNA chain linked thereto.
13. The RNA according to 12 above wherein selected RNA chain is a ribozyme or an antisense RNA.
14. The RNA according to 12 above wherein a bulge structure is formed with any nucleotide of an RNA chain linked to the 3' terminus and any nucleotide of the region of nucleotides 8 to 14 within the nucleotide sequence of an RNA adopting secondary structure (I).
15. An expression vector comprising DNA encoding the RNA of 12 above.

Having consideration for the transcription amount, stability and post-transcription activity of ribozymes, we selected human tRNA$^{Val}$ promoter which is involved in a polymerase III system, as an expression system therefor, and examined whether there was any difference in ribozyme effect in vivo due to the way in which the ribozyme was linked to this promoter. In other words, we focussed on intracellular stability which is an important factor in obtaining significant ribozyme effect in vivo, and post-transcription activity, and set out to clarify the relationship between the high-order structure of ribozymes and these factors.

First, we designed a hammerhead ribozyme targeting a relatively conserved sequence of HIV-1, and constructed four expression systems by attaching this gene to downstream of the tRNA$^{Val}$ promoter via various sequences. As a vector for the construction of these expression systems we used pUC19 (Takara), however, other vectors such as pGREEN LANTERN (Life Technologies Oriental, Inc.) and pHaMDR (HUMAN GENE THERAPY 6:905–915 (July 1995)) may also be used. Also, oligonucleotide sequences necessary for the construction of these expression systems can be chemically synthesized with a DNA/RNA synthesizer (Model 394; Applied Biosystems, Division of Perkin Elmer Co. (ABI), Foster City, Calif.).

From predictions made using Zuker's method, it was thought that differences in the linker sequence used to connect the tRNA$^{Val}$ promoter and hammerhead ribozyme would exert great influence on the secondary structure of the recognition site of the ribozyme (See FIG. 1). According to this prediction map, it was clear that whereas the overall secondary structure of the ribozyme was almost the same, the degree of freedom at the substrate-binding site differed greatly. It is clear that whereas both substrate binding sites form a stem structure within the molecule in Rz1, one binding site in Rz2, and both binding sites in Rz3 protrude to the outside. In the case of Rz3, the protruding substrate binding site may be masked by protein. However, since a ribozyme is an RNA enzyme and both binding ability and disassociation ability with a substrate are important factors in its activity. Rz3 was expected to be the best in terms of cleavage ability. We performed a reaction using intracellularly transcribed ribozymes, in an in vitro system under the following conditions: 40 mM Tris-Cl (pH8.0), 8 mM MgCl$_2$, 5 mM DTT, 2 mM Spermidine, 2 U/μl RNase inhibitor, 30 μg total RNA. At this time, the ribozyme content in total RNA was made constant. The results showed that ribozyme activity toward short substrates that were transcribed in vitro and radioactively labeled depended on the degree of freedom at the recognition site (See FIG. 2). Further, stability of the ribozymes was examined, with the expression amount of a control gene made constant, we conducted a comparative study of each ribozyme amount. The difference in ribozyme structure also affected stability. The reason why structures having such little overall difference exert this influence is not clear, however, a difference of approximately 25 times was exhibited as between the most stable and the least (FIG. 3B).

We next examined the relationship between ribozyme activity in vitro and in vivo effect, which as discussed above is as yet unclear. First, using a luciferase gene as a reporter gene, a system for evaluating ribozyme effect was constructed wherein ribozymes are allowed to act on a fusion gene of this reporter gene and the sequence pNL4-3 (an HIV-1 clone), and luciferase activity in the cell extract is measured (See FIG. 3A). A comparison of each of the ribozymes showed that the one with the highest intracellular stability exhibited highest activity suggesting the importance of stability (See FIG. 4).

The above discussion relates to an evaluation of ribozyme effect on an artificial fusion gene of a luciferase gene and a HIV-1 sequence, in cultured cells. Therefore, it may be difficult to judge that these results are the equivalent of results that could be obtained in an organism. Thus, we performed an evaluation of ribozyme effect against actual HIV-1 (See FIG. 5). A ribozyme expression system transformant was infected with HIV-1, and virus growth was measured by measuring the amount of p24 (core protein of the virus) produced in serum. Results indicating a similar trend to our evaluation in cultured cells were obtained. Further, it was clear that the ribozyme with the highest in vitro stability exhibited very high inhibitory effect with production of p24 inhibited by 99% (See FIG. 6C). In contrast, the ribozyme expression system having the highest cleavage activity in vitro was mostly unable to inhibit growth of the virus.

In this manner it became clear that the evaluation of ribozyme effect with the virus indicated the same trend as the evaluation with the artificial substrate in cultured cells. Thus, the results of the once-over evaluation we performed are thought to be a rough guide to the effect of the ribozymes in vivo. Further, from the results of these experiments both in vitro and those dealing with a virus, it is clear that to obtain significant intracellular effect of the ribozyme, while activity is important, intracellular stability is of greater importance. The fact shown in the case described herein, that even ribozymes whose sequences have little differences lead to great differences in effect in vivo depending on the linkage to the expression system, must be fully considered. The above result also suggests that it is important to design ribozymes with high stability while considering the influence of higher structures comprising added sequences for expression on their stability.

tRNA is first recognized intracellularly with its promoter sequence consisting of sequences known as A box and B box within its structural sequence, and transcribed with the extra sequences connected to the 5' and 3' ends. Next, with to the action of a plurality of mature enzymes which exist within cells, extra sequence are eliminated to form mature tRNA. In the action of these enzymes, the structure of the portion known as the amino-acyl stem becomes an important determinant of structure recognition. We found that by establishing a small bulge structure at the portion, it was possible to avoid the action of the mature enzyme. For example, in FIG. 1, each of Rz1, Rz2 and Rz3 has a small bulge structure at the amino-acyl stem, and as a result, the ribozyme sequence of the transcribed RNA is not eliminated (FIGS. 3B, 7A and determined base sequence). Such a property is not due to the 3' end sequence being a ribozyme but is due to the bulge structure at the amino-acyl stem portion, consequently, any RNA sequence comprising antisense may be used.

Typically tRNA undergoes a series of processings before transportation from the nucleus including the removal of extra sequences at the 5' and 3' ends by a mature enzyme, removal of any introns by splicing mechanism, modification of specific bases, and addition of a sequence consisting of 5'-CCA-3' to the 3' terminus and, in some cases addition of amino acids suitable for said tRNA (amino-acylation).

However, the tRNA of the present invention is actively transported out of the nucleus without being subject to, from among the above series of modifications, at least, removal of extra sequences at the 5' and 3' ends, addition of a CCA sequence to the 3' end, and subsequent amino acylation (FIG. 7A). This is likely because establishing a bulge in the amino acyl stem portion results in avoidance of action by mature enzymes and following addition of CCA sequence followed by amino acylation, and the entire structure resembles that of the original tRNA. This inference was also supported by the fact that the one with degenerated tRNA structure (Rz4), according to structure predictions using computers, was not transported to the cytoplasm. (FIG. 7C). This property of being transported from the nucleus to the cytoplasm does not depend on the ribozyme sequence at the 3' end, and thus it is thought that any RNA sequence such as antisense RNA may be used similarly.

In recent years, it has come to be understood that where antisense RNA and ribozyme RNA are expressed intracellularly, in order to elicit their function, it is important that their distribution in a cell is within the cytoplasm. Since RNAs of the present invention form stable tRNA-like structures by themselves, they have the function of definitely transporting to the cytoplasm without exerting great influence on the higher-order structure of the RNA linked to the 3' end (which is an extremely important property when the RNA linked to the 3' end is a functional RNA such as a ribozyme or antisense RNA). Further, when the RNA is made into DNA, it functions as a promoter irrespective of cell type and it has a broad range of hosts (originally of human derivation, but should be able to express in at least all mammals.) In short, the present invention is most suitable for an antisense RNA and ribozyme RNA expression systems, and can become an important tool for experiments using cultured cells and for gene therapy in the field of medicine. Further, through the technique of molecular evolution engineering, RNA molecules with functions not found in nature, are recently being artificially created. If these molecules exhibit their functions intracellularly, particularly in the cytoplasm, then the present invention will be able to be used as an expression system for these RNA molecules.

Using the tRNA$^{Val}$-ribozyme of the present invention it is possible to specifically cleave a target RNA, particularly an HIV-1 RNA.

The tRNA$^{Val}$-ribozyme of the present invention can be used as a medicine especially for the prevention and/or treatment of acquired immune deficiency syndrome. For example, the transcription of HIV can be inhibited by encapsulating the tRNA$^{Val}$-ribozyme of the present invention in a liposome, administering this to an organism and allowing incorporation into cells comprising HIV. Further, transcription of HIV can be inhibited by incorporating DNA encoding the tRNA$^{Val}$-ribozyme of the present invention in a vector such as virus, introducing the vector into cell comprising HIV to allow intracellular expression of the vector thereby effecting production of the tRNA$^{Val}$-ribozyme of the present invention. Administration of the tRNA$^{Val}$-ribozyme of the present invention will depend on severity of the conditions of the patient and responsiveness of the organism, and may be conducted in appropriate amount, form of administration and frequency, and over a period until the efficacy of prevention and/or treatment can be recognized, or until alleviation of the patient's condition is achieved.

The present specification incorporates in its entirety the content of the specification and drawings of Japanese Patent Application No. 10-244755, said application forming the basis of the priority claim of this application.

BEST MODE FOR CARRYING OUT THE INVENTION

Figure 1:
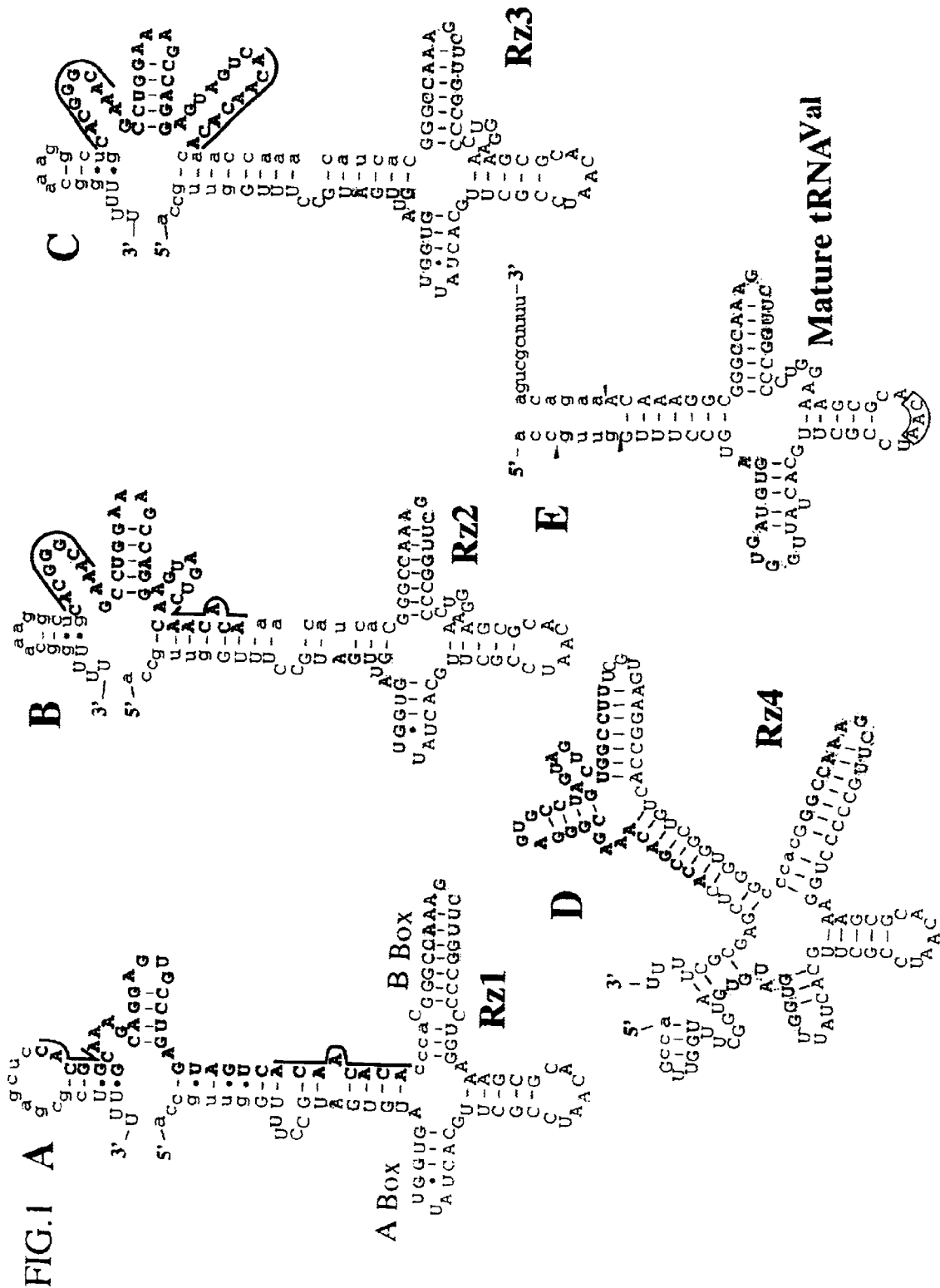
FIGS. 1(A–E) shows the secondary structures of tRNA$^{Val}$-ribozymes that were predicted by computer folding. The sequence of hammerhead ribozyme (bold capital letters) was ligated with that of tRNA$^{Val}$ sequence (capital letters) by means of various linker sequences. The sequences that correspond to the internal promoter of seven-base-deleted tRNA$^{Val}$, namely the A and B boxes, are indicated by shaded boxes. Diagrams A to D show the secondary structures of tRNA$^{Val}$-ribozyme 1 (Rz1), 2 (Rz2), 3(Rz3) and 4(Rz4), respectively. The recognition arms of ribozymes are indicated by underlining. Diagram E shows the secondary structure of the transcript of human placental tRNA$^{Val}$. The tRNA is processed at three sites (arrowheads) to yield in the mature tRNA$^{Val}$ (capital letters).

Below, the present invention will be explained in further detailed by means of examples. However, this is not intended to limit the scope of the present invention to these examples.

EXAMPLES

Materials and Methods

Construction of Plasmids

The plasmids (pUCdt-Rz series) that expressed each tRNA$^{Val}$-ribozyme were constructed as follows. Both sense and antisense oligonucleotide linkers encoding the sequence of the promoter region, derived from the human gene for placental tRNA$^{Val}$(pHtV1; Arnold et al., 1986), were annealed and ligated into the EcoRI/SalI site of pUC19. The sequences of the oligonucleotide linkers were as follows: sense, 5'-aat tca gga cta gtc ttt tag gtc aaa aag aag aag ctt tgt aac cgt tgg ttt ccg tag tgt agt ggt tat cac gtt cgc cta aca cgc gaa agg tcc ccg gtt cga ag-3' (SEQ ID NO: 6): antisense, 5'-tcg act tcg aac cgg gga cct ttc gcg tgt tag gcg aac gtg ata acc act aca cta cgg aaa cca acg gtt aca aag ctt ctt ctt ctt ttt gac cta aaa gac tag tcc tg-3' (SEQ ID NO: 7). Next, both sense and antisense oligonucleotide linkers that encoded the terminator sequence were also annealed and ligated into the NspV/SalI site of pUC19 that contained the sequence of the promoter region. The sequences of oligonucleotide linkers were as follows: sense, 5'-cga aac cgg gca ccc ggg gaa tat aac ctc gag cgc ttt ttt tct atc gcg tc-3' (SEQ ID NO: 8);antisense, 5'-tcg acg cga tag aaa aaa agc gct cga ggt tat att ccc cgg gtg ccc ggt ttc-3' (SEQ ID NO: 9). The resultant plasmid which contained the A and B boxes of tRNA$^{Val}$ and a terminator, was designated pUCdt.

DNA fragments encoding the sequence of each ribozyme and the tRNA$^{Val}$ portion were amplified by PCR using pUCdt as a template with an upper primer (5'-cgc cag ggt ttc cca gtc acg ac-3') (SEQ ID NO: 10) and a lower primer that included the sequences of both the ribozyme and the terminator (Rz1, 5'-ctg cag gtc gac gcg ata gaa aaa aag cgc tcg agg tgc ccg ttt cgt cct cac gga ctc atc agt gtt gtg tgg gtg ccc ggt ttc gaa ccg gga cct tt-3' (SEQ ID NO: 11); Rz2, 5'-ctg cag gtc gac gcg ata gaa aaa aac cgt ttc cga cgt gcc cgt tcc ggt cct ttc ggt cct cat cag tgt tgt gtt tgt agt gcc cgg ttt cga acc ggg gac ctt t-3' (SEQ ID NO: 12); Rz3, 5'-ctg cag gtc gac gcg ata gaa aaa aac cgt ttc cga cgt gcc cgt tcc ggt cct cat cag tgt tgt gtg ttg gtt tgt agt gcc cgg ttt cga acc ggg gac ctt t-3' (SEQ ID NO: 13)). After digestion of products of PCR with the EcoRI and SalI, each fragment was ligated into the EcoRI/SalI site of pUC19 to yield pUCdt-Rz. The sequences of pUCdt and pUCdt-Rz series were confirmed by direct nucleotide sequencing. The members of pUC-Rr series, which contained a reference gene-expression cassette in addition to the gene for the tRNA$^{Val}$-ribozyme (see FIG. 3A), were constructed by inserting the PvuII fragment of pUCdt into the HincII site of each pUCdt-Rz. The direction of the inserted fragment was confirmed by digestion with restriction enzymes. The pHyg dt-Rz series, which was used for generation of the ribozyme-transduced HeLa cells, was constructed by inserting each PvuII-SalI fragment of the pUCdt-Rz series into the EcoRV/SalI site of pHyg (Yates et al., 1984). All oligonucleotide linkers and primers for PCR were synthesized by a DNA/RNA synthesizer (model 392; PE Applied Biosystems, Foster City, Calif.).

Figure 5:
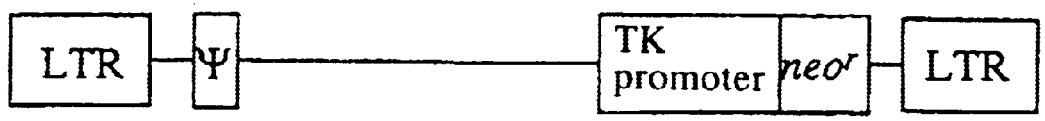
FIGS. 5(A and B) is a schematic representation of the HIV vector. The expression cassette for each tRNA$^{Val}$-ribozyme was inserted into the SalI site immediately upstream of TK-neo$^r$ in HIV-I-derived vector (A) to yield a retroviral vector, HIVRibo.N, that encoded a tRNA$^{Val}$-ribozyme(B). ψ indicates a packaging signal.
Figure 5:
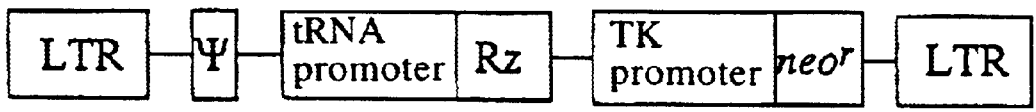

Recombinant HIV vector plasmids were constructed as follows. A 2.0-kbp BamHI fragment that encoded the bacterial neo$^r$ gene cassette from PMC1 neo (Thomas and Capecchi, 1987) was inserted into the SalI site of an HIV-1-derived vector (FIG. 5A; Shimada et al., 1991). Then, the tRNA$^{Val}$-ribozyme expression cassette was cloned into the SalI site, immediately upstream of TK-neo$^r$, as shown in FIG. 5B.

Culture and Transfection of Cells

HeLa and Cos cells were cultured in Dulbecco's modified Eagle's medium (DMEM; Gibco BRL, Gaithersburg, Md.) supplemented with 10% (v/v) fetal bovine serum (FBS; Gibco BRL) and 45 µg/ml gentamycin (Gibco BRL). To select ribozyme-transduced cells, hygromycin B was used at a final concentration of 300 µg/ml. H9 cells were cultured in RPMI (Gibco BRL) supplemented with 10% fetal calf serum (FCS; Gibco BRL).

Cells were transfected using the Lipofectin reagent (Gibco BRL) according to the manufacturer's protocol. A recombinant HIV vector plasmid (HIVRib.N; shown in FIG. 5B) was used to transfect H9 cells by the CaPO$_4$ co-precipitation.

Preparation of RNA

Total RNA was extracted by the guanidinium thiocyanate-phenol-chloroform-method. Cytoplasmic RNA and nuclear RNA were separated as described previously (Huang and Carmichael, 1996).

Measurement of the Steady-state Levels and Half-lives of Ribozymes

Figure 3:
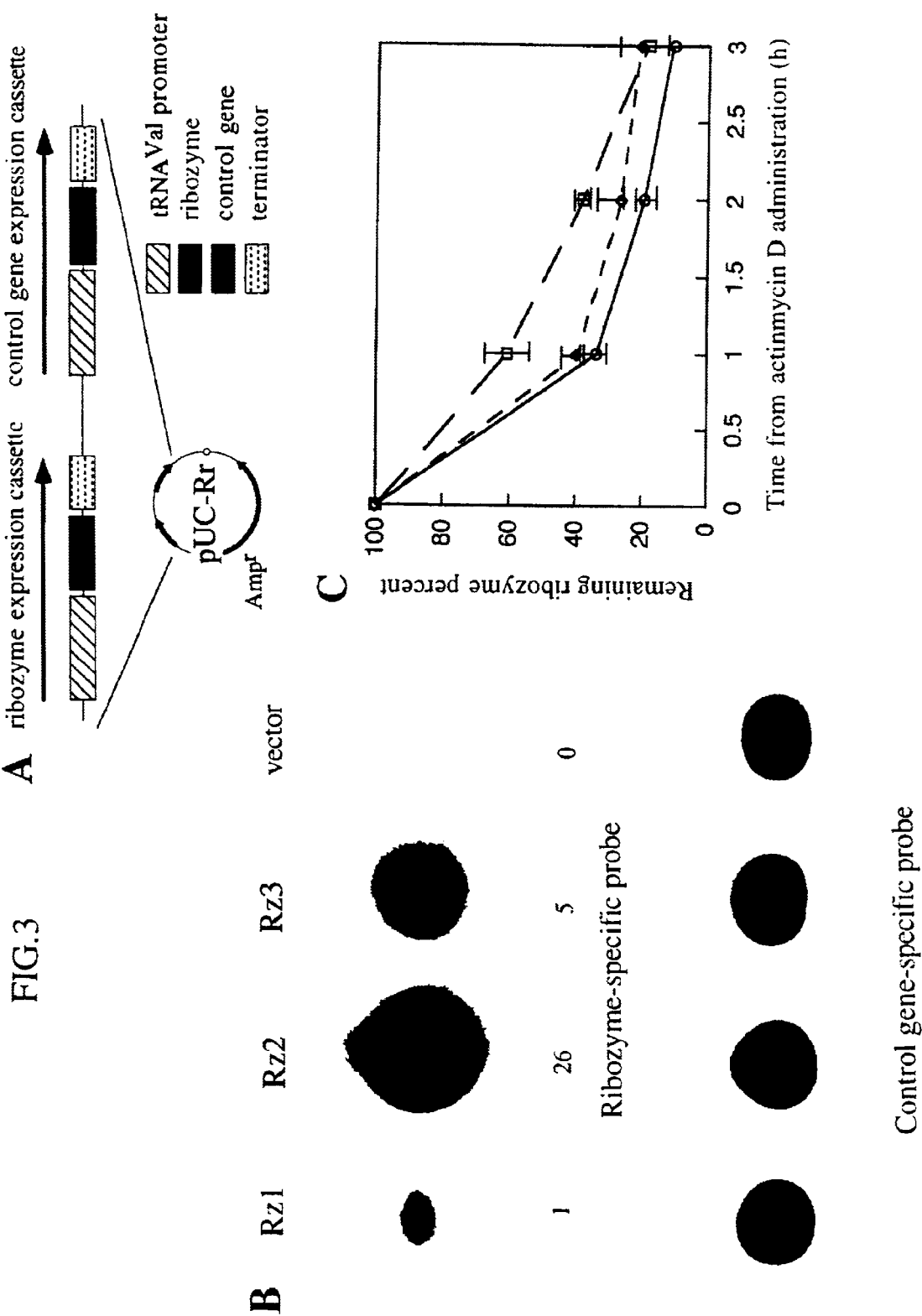
FIGS. 3(A–C) indicates the stability of tRNA$^{Val}$-ribozyme in vivo. Panel A is a schematic representation of pUC-Rr that allowed normalization of the efficiency of transfection by the use of a reference gene. The reference gene was expressed downstream of the ribozyme-expression cassette. The sequences of the promoter and terminator were the same, respectively, in the two expression cassettes. Panel B shows steady-state levels of expression of tRNA$^{Val}$-ribozyme. This figure shows Northern blotting analysis with the probe specific for the ribozyme (upper) and for the reference gene (bottom) Figure C indicates the half-lives of tRNA$^{Val}$-ribozymes in stably ribozyme-transduced cells. The circles indicate relative amounts of tRNA$^{Val}$-ribozyme 1 (Rz1). Squares and diamonds indicate relative amounts of ribozyme 2 (Rz2) and 3 (Rz3), respectively. Bars show S.E. of results from 3 assays.

The steady-state level of each ribozyme was measured as follows. HeLa cells (1×10$^6$ cells/10-cm plate) were transfected with each pUC-Rr. Two days after transfection, total RNA was isolated from these cells. The amount of the reference RNA, located downstream of tRNA$^{Val}$-ribozyme in the isolated total RNA, was quantified first by Northern blotting analysis with a probe specific for the reference RNA (5'-aaa tcg cta taa aaa gcg ctc gag gtt atg ctc ccc ggg t-3') (SEQ ID NO: 14). The amount of the reference DNA in each sample was maintained at a constant value and the level of total RNA in each sample was also kept constant by addition of RNA isolated from untransfected HeLa cells as necessary. Finally, hybridization was repeated with a probe specific for the ribozyme (5'-ctc atc tgt gtt gtg t-3') (SEQ ID NO: 15) or the probe specific for the reference RNA (FIG. 3B).

The half-life of each ribozyme was determined by Northern blotting analysis after treatment of cells with actinomycin D as described previously (Huang and Gerlach, 1996). In brief, cells were exposed to actinomycin D at a final concentration of 5 µg/ml for 0, 60, 120 or 180 min and, at each time point, total RNA was isolated (FIG. 3C). The amount of ribozyme in each preparation of isolated RNA was determined by Northern blotting.

Cleavage Assay

Total RNA was isolated from HeLa cells transfected with each pUCdt-Rz or pUCdt The amount of ribozyme in each preparation of isolated RNA was determined by Northern blotting with the probe that was specific for the ribozyme. Then the concentration of each ribozyme was adjusted to the same value by addition of RNA isolated from untransfected HeLa cells. The substrate RNA that encoded the U5 LTR region of HIV-1 (FIG. 2A) was prepared by T7 transcription and radiolabeled with $^{32}$P. cleavage reactions were allowed to proceed in a 50 µl reaction mixture [40 mM Tris-HCl (pH 8.0), 8 mM MgCl$_2$, 5 mM dithiothreitol (DTT), 2 mM Spermidine, 40 U of placental RNase inhibitor, 30 kg of total RNA, 5kcpm of radiolabeled substrate RNA] at 37° C. for 12 h. Products were identified after electrophoresis on 6% polyacrylamide gel/7M urea gel (FIG. 2B).

Luciferase Assay

Figure 4:
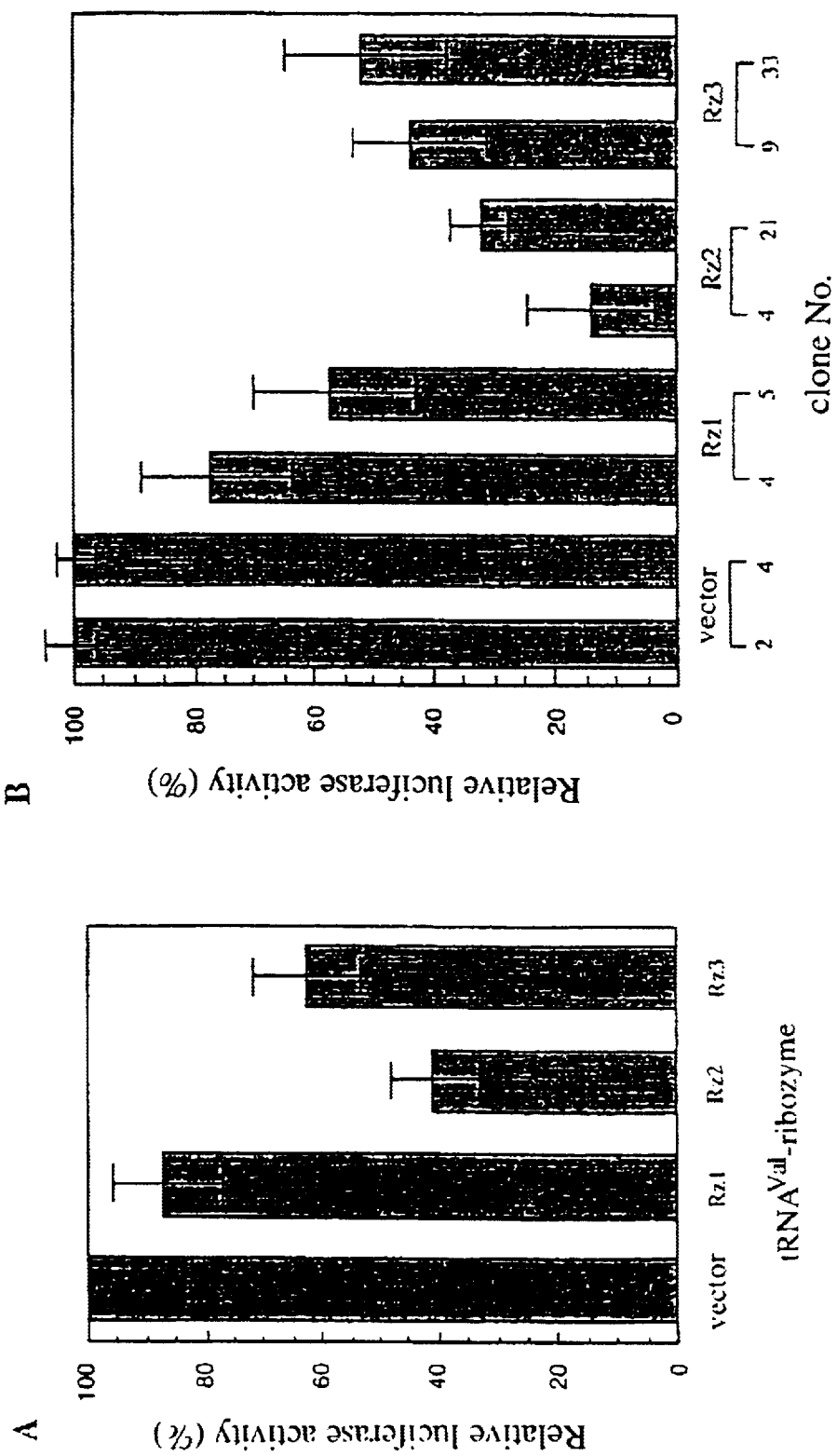
FIGS. 4(A and B) shows the inhibition of production of the U5 LTR-luciferase fusion gene in HeLa cells. Panel A. Transient expression in HeLa cells. Both the target-expressing plasmid and pUCdt-Rz encoding a ribozyme were used to co-transfect HeLa cells. Panel B. Transient expression in stably ribozyme-transduced cells. Two independent clones were selected for each construct with similar levels of transcription of the inserted gene tRNA$^{Val}$ or tRNA$^{Val}$-ribozyme). Only the target-expressing plasmid was used to transfect ribozyme-producing HeLa cells. Bars show S.E. of results from 5 assays.

Luciferase activity was measured with the Dual-Luciferase™ Reporter Assay System (Promega. Madison, Wis.) according to the manufacturer's protocol. HeLa cells transfected with pUCdt-Rz and the target-expressing plasmid (FIG. 4A) or ribozyme-producing HeLa cells that had been transduced with the target-expressing plasmid (FIG. 4B) were lysed in 150 µl of 1× Passive lysis buffer for 15 min and scraped off the plate. The cell debris was removed by centrifugation. After addition of 20 µl of the centrofuged lysate to 100 µl of Luciferase Assay Reagent II, the luminescent signal was immediately quantitated with a luminometer (Lumant LB 9501; Berthold, Bad Wildbad, Germany). Furthermore, for normalization of the activity of firefly luciferase, we measured the luminescent signal generated by Renilla luciferase by adding 100 µl of Stop & Glo™ Reagent to the sample tube immediately after quantitation of the reaction catalyzed by firefly luciferase. The recorded value of firefly luciferase activity was normalized by reference to the activity of Renilla luciferase (FIG. 4).

Each normalized value of firefly luciferase activity was further normalized by reference to the concentration of protein in the lysate. The protein was quantitated with a Protein Assay Kit (Bio-Rad, California, USA) which was based is Bradford's method.

HeLa Cells Stably Transduced With a Ribozyme

Ribozyme-transduced cells were obtained by transfecting HeLa cells with pHyg dt or a member of the pHyg dt-Rz series and selection in DMEM that contained 300 µg/ml hygromycin B (Waco Chemicals, Osaka, Japan). Twelve h after transfection, the medium was replaced by growth medium and the cells were cultured for another 48 h. The cells were subcultured at a dilution of 1:5 in DMEM that contained 300 µg/ml hygromycin B (selection medium). The medium was replaced by fresh medium every three days. Cells resistant to hygromycin B were expanded in DMEM that contained 250 µg/ml hygromycin B.

Production of Virus and Transduction of the Ribozyme by an HIV Vector

A supernatant containing recombinant virus was produced as described previously (Shimada, 1991). Cos cells (2×10$^6$ cells/10-cm dish) were cultured and transfected with 10 µg of the packaging vector plasmid and 10 µg of the recombinant HIV vector plasmid (HIVRib.N; shown in FIG. 5). The supernatant, which contained recombinant virus, was collected after 48 h and filtered through a 0.22 µm pore filter. Then 2×10$^4$ H9 cells were incubated with 5 ml of the filtered supernatant that contained 6 µg/ml Polybrene™ (Abbott Laboratories). After 24 h, the medium was replaced with RPMI supplemented with 10% FCS and 1 mg/ml G418.

These cells were cultured for a further 48 h and then G418-resistant clones were isolated. The transduction of the ribozyme gene was confirmed by RT-PCR analysis.

Quantitation of tRNA$^{Val}$-ribozyme Produced in H9 Cells

Quantitative RT-PCR was carried out as follows (Ozawa et al., 1990; Hamblet and Castora, 1995). Total RNA was extracted from H9 cells that had been stably transduced with a ribozyme. cDNA was synthesized in a 20-µl reaction mixture [1 µg of total RNA, 20 mM Tris-HCl (pH 8.3), 50 mM KCl, 5 mM MgCl$_2$, 1 mM dNTP, 1 pmol of primer(for β-actin, 5'-gtg gcc atc tct tgc tcg aa-3' (SEQ ID NO: 16); for ribozyme: 5'-gac ctt tcg gtc ctc atc-3' (SEQ ID NO: 17)) and 0.25 U/ml Moloney murine leukemia virus Rtase (Takara Shuzo, Kyoto, Japan)) at 42° C. for 30 min.

cDNA for β-actin was amplified by PCR with two oligo-nucleotide primers (upper, 5'-gac tac ctc atg aag atc ct-3' (SEQ ID NO: 18); lower: 5'-gtg gcc atc tct tgc tcg aa-3' (SEQ ID NO: 19)) with 13, 15 or 17 cycles of 94° C. for 1 min, 60° C. for 1 min and 72° C. for 2 min. Ribozyme cDNA was amplified by PCR with two oligonucleotide primers (upper, 5'-gtt atc acg ttc gcc taa-3' (SEQ ID NO: 20); lower: 5'-gac ctt tcg gtc ctc atc-3' (SEQ ID NO: 21)) with 13, 15 or 17 cycles of 94° C. for 1 min 55° C. for 1 min. and 72° C. for 2 min.

Products of PCR after 13, 15 and 17 cycles were analyzed by Southern blotting with a radiolabeled probe specific for the ribozyme (5'-acg cga aag gtc ccc ggt-3' (SEQ ID NO: 22)) or for β-actin (5'-gcg gga aaa tcg tgc gtg a-3' (SEQ ID NO: 23)) The radioactivity of each band (FIGS. 6A and 6B) was measured with BAS2000 system (Fuji Film, Tokyo, Japan).

HIV-1 Challenge Assay

H9 cells transduced with the ribozyme by the HIV vector (HIVRib.N) and mock-tranduced control cells were incubated with NL432 at a m.o.i. (multiplicity of infection) of 0.01 for 4h. After two washes with PBS, these cells were cultured at 1×10$^5$ cells/ml in RPMI 1640 medium supplemented with 10% FCS. The supernatant was collected on days 3, 7, and 11 after viral infection. The level of the p24 antigen of HIV-1 in each supernatant was determined with an HIV-I antigen-capture ELISA test kit (DAINABOT, Tokyo, Japan) according to the manufacturer's protocol.

Results

Secondary Structures of tRNA$^{Val}$-ribozymes and Their Cleavage Activities in vitro To construct a pol III-driven ribozyme-expression cassette, we cloned a ribozyme sequence targeted to the 5' leader sequence of HIV-1 RNA (Adachi et al., 1986; Yu et al., 1993) adjacent to the sequence of a tRNA$^{Val}$ promoter, with three kinds of short linker between them (linker sequences are indicated by lowercase letters and ribozyme sequences are indicated by bold capital letters in FIG. 1), to yield a set of pUCdt-Rz plasmids. The insertion of the short linkers changed the overall structure of the transcripts and, thus, affected the accessibility of the recognition arms of the ribozyme (recognition arms are underlined). Naturally, it is important that both the 5' and 3' substrate-recognition arms of the ribozyme be available to the substrate so that the ribozyme can form the stem structures with the substrate RNA that ensure subsequent cleavage of the substrate. In order to clarify the relationship between structure and functional activity, we chose linkers that altered the extent of availability of the recognition arms. FIG. 1 shows the secondary structures of the tRNA$^{Val}$-ribozymes (sequences corresponding to A and B boxes are shaded), as predicted by computer modeling (Mulfold Biocomputing Office, Biology Department. Indiana University, IN, USA). In one case (FIG. 1A), the linker was inserted before the terminator sequence and restricted the flexibility of the 3' substrate recognition arm of the ribozyme. In addition, the 5' substrate-recognition arm was unavailable. Therefore, in the case of tRNA$^{Val}$-ribozyme 1 (Rz1 in FIG. 1A), both 5' and 3' substrate-recognition arms were mostly embedded in a helical structure. tRNA$^{Val}$-ribozyme 2 (Rz2) has one restricted substrate-recognition arm on the 5' side. By contrast, tRNA$^{Val}$-ribozyme 3 (Rz3) had no restricted substrate-recognition arms and both arms were available for binding to the substrate. Judging from the flexibility of the substrate-recognition arms, we might expect that the cleavage activity of Rz3 would be the highest, followed by Rz2 and Rz1 in that order. The base sequences of Rz1–3 are represented in SEQ ID NOS: 3, 1 and 2, respectively.

Figure 2:
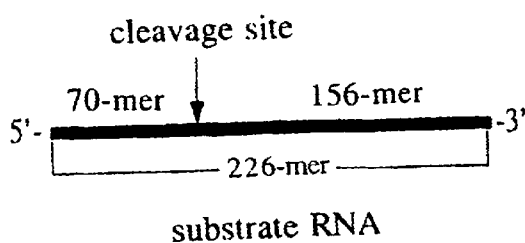
FIGS. 2(A and B) indicates the cleavages mediated by tRNA$^{Val}$-ribozyme in vitro. Panel A is a schematic representation of the substrate RNA (the substrate RNA corresponds to nucleotides 500–711 of pNL432, namely the U5 region of HIV-1 RNA). The substrate RNA was cleaved into two fragments by the tRNA$^{Val}$-ribozyme (5' fragment, 70-mer; 3' fragment 156-mer). Panel B is an autoradiogram showing the results of cleavage reactions. Lanes; M, markers; vector, tRNA$^{Val}$ vector alone without a ribozyme; Rz1—ribozyme 1; Rz2—ribozyme 2; and Rz3—ribozyme 3.
Figure 2:
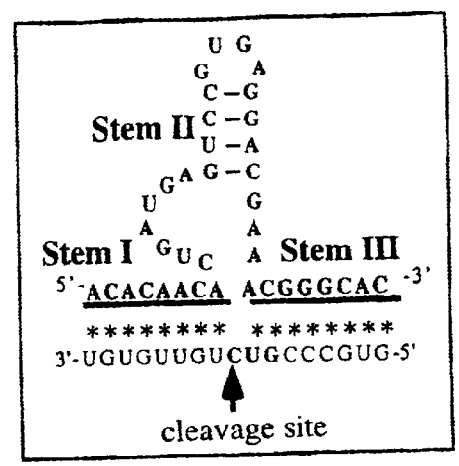
Figure 2:
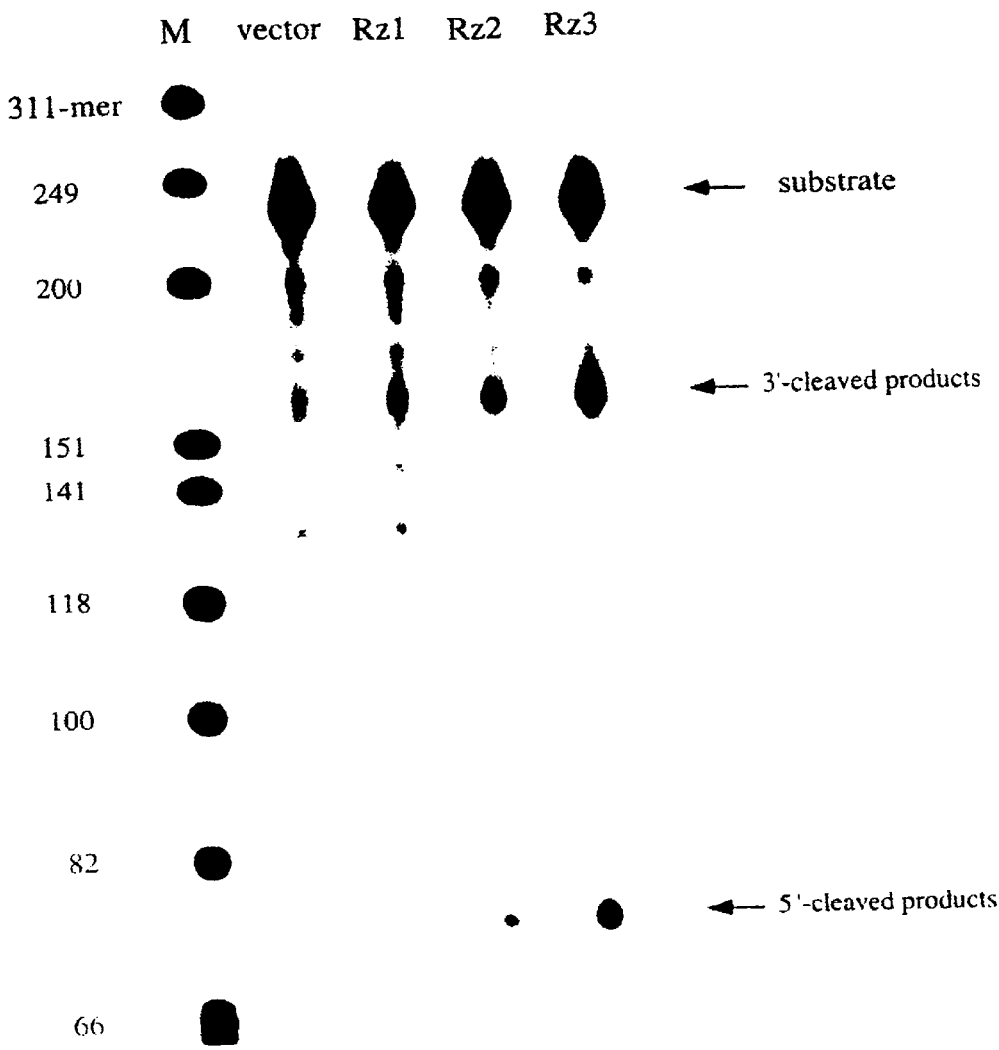

To examine whether the above ribozymes had the cleavage activity that we predicted from their secondary structures, (FIG. 1) we first compared activities in vitro. Total RNA was isolated from HeLa cells that had been transfected with various pUCdt-Rz, plasmids that encoded the above ribozymes (tRNA$^{Val}$-ribozyme). We mixed a fixed amount (based on Northern blotting data) of each ribozyme within the isolated RNA and radiolabeled substrate RNA to initiate the cleavage reaction, and we monitored the progress of each reaction, after a 12-h incubation, on a 6% polyacrylamide/7 M urea gel (FIG. 2). As expected, the cleavage activity of Rz3, with both recognition arms available, was the highest, followed by that of Rz2, while that of Rz1, with both recognition arms unavailable, was very low. It was, therefore, clear that the cleavage activity of tRNA$^{Val}$-ribozymes in vitro could be deduced from their computer-generated secondary structures.

Steady-state Levels and Half-lives of tRNA$^{Val}$-ribozymes

We expected that minor structural changes would occur in the entire structure as a result of the linker sequence. Thus, the linker should exert considerable influence on the stability of each ribozyme in vivo. We compared the intracellular stability of each tRNA$^{Val}$-ribozyme using two different approaches, as follows. We compared the steady-sate level of each transcript from HeLa cells that had been transiently transfected with pUC-Rr (a sequence of a reference gene was added to each ribozyme-coding pUCdt-Rz plasmid to yield pUC-Rr; FIG. 3A) by Northern blotting analysis (transient expression assay). The level of expression of each tRNA$^{Val}$-ribozyme was normalized by adjusting the amount of the transcript of the reference gene, which was connected, in tandem, in the same plasmid (pUC-Rr; FIG. 3A). Transcripts of about 150 nucleotides in length (corresponding to the size of chimeric tRNA$^{Val}$-ribozyme) were detected in all samples of RNA that we isolated from HeLa cells that had been transfected with each plasmid that encoded a tRNA$^{Val}$-ribozyme. The steady-state levels of the tRNA$^{Val}$-ribozymes differed over a 30-fold range of concentration. The level of Rz2, which was the highest, was about 26 times that of Rz1, which was the lowest, and the level of Rz3 was about 5 times that of Rz1. Since no modifications had been made in the promoter region of each ribozyme-expression cassette and, thus, since the efficiency of transcription was assumed to be the same in each case, we postulated that these differences among steady-state levels of transcripts were a consequence of the stability in vivo of each respective transcript.

As a second approach and to test the above hypothesis, we attempted to compare the stability of each transcript under more natural, intracellular conditions. We established stable HeLa transformants that produced each tRNA$^{Val}$-ribozyme and measured the intracellular half-life of each transcript directly by interrupting cellular transcription with actinomycin D. As shown in FIG. 3C, the rate of degradation of Rz2 was lower than those that of Rz1 and of Rz3. The half-life of Rz2 (100±10 min) was more than twice that of Rz1 (35±2 min) and Rz3 (40±15 min). These results were in good agreement with the results of the transient expression assay and supported our hypothesis that the difference in the steady-state level of transcripts was due to the stability in vivo of each transcript rather than to any differences in the efficiency of transcription.

Intracellular Activities of tRNA$^{Val}$-ribozymes

In order to evaluate the intracellular activities of the tRNA$^{Val}$-ribozymes, we performed two types of assay. We first used each tRNA$^{Val}$-ribozyme expression plasmid (pUCdt-Rz) and a target gene expression plasmid, which encoded a chimeric HIV-1 LTR (R-U5 region)-luciferase gene, to co-transfect HeLa cells. After transient expression of both genes, in each cell lysate, we estimated the intracellular activity of each tRNA$^{Val}$-ribozyme by measuring the luciferase activity. The luciferase activity recorded when we used the control plasmid (pUCdt), with only minimal tRNA$^{Val}$ promoter and terminator sequences instead of the ribozyme-expression plasmid, was taken as 100%. As shown in FIG. 4A, Rz2, which had the highest stability in vivo, was most effective (>60% inhibition), followed by Rz3 (>40% inhibition). Rz1 was not very effective (about 10% inhibition), as expected from its low cleavage activity in vitro (FIG. 2B) and low stability in vivo (FIGS. 3B and 3C).

In the second assay, only the target gene-expressing plasmid was used to transfect stable transformants that produced almost identical levels of tRNA$^{Val}$-ribozyme (stable HeLa transformants had been picked up arbitrarily and those clones with almost identical levels of expression of the ribozyme were selected for these studies). In this experiment (FIG. 4B), with two independent stable transformants for each ribozyme, we observed a similar trend to that described in the preceding paragraph. However, in this case, the effects of all of the ribozymes were stronger, most probably because all the transformed HeLa cells produced tRNA$^{Val}$-ribozyme constitutively. Rz2 inhibited expression of the target gene to a significant level, in some cases by as much as 97%.

Although Rz3 had the highest cleavage activity in vitro, it failed to act more effectively than Rz2 in the cellular environment. These results suggest that, if a transcribed ribozyme is sufficiently stable within the cell, even if it does not have extremely high cleavage activity, it can have a remarkable effect in vivo.

The Ability to Inhibit Replication of HIV-1

Since the above described studies demonstrated that Rz2 and Rz3 might have significant cleavage activity against the sequence of HIV-1 in vivo, we compared the abilities of that RNA$^{Val}$-ribozyme to inhibit replication of the HIV-1. Using an HIV vector (FIG. 5; shimada et al., 1991), we obtained stable transformants of the H9 cell line that expressed Rz2 or Rz3 (since Rz1 was inactive in studies described above, we above, we made no attempts to isolate stable transformants that produced Rz1). Cells transduced with the HIV vector without a ribozyme-expression cassette (FIG. 5A) were used as a mock control. Two independent cell lines were used for subsequent analysis, and we detected no obvious changes in their growth rates over a period of 11 days, as compared with that of calls that did not produce either ribozyme (data not shown). Therefore, the ribozymes were not detrimental to host cells and probably only cleaved their target RNA with high specificity (Kawasaki et al., 1996, 1998).

Figure 6:
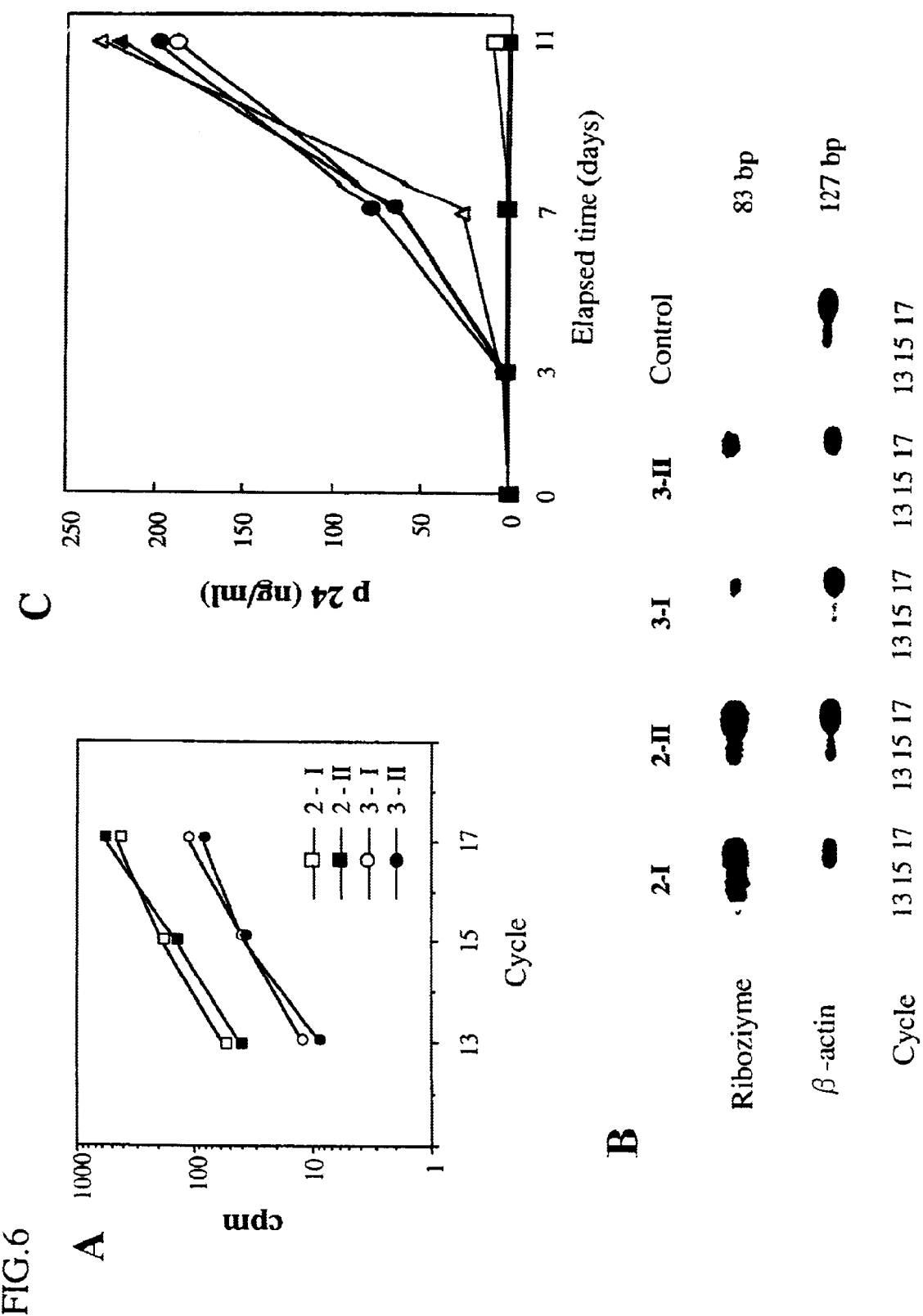
FIGS. 6(A–C) shows quantitation of the expression of tRNA$^{Val}$-ribozyme in stably ribozyme-transduced H9 cells (CD4+ T cells) and inhibition of production of p24 in the transduced cells. Panel A. Quantitation of results, shown in B, of Southern blotting analysis of the RT-PCR-amplified ribozyme from two independent clones of ribozyme-transduced H9 cells. Products of PCR after 13, 15, and 17 cycles were analyzed by Southern blotting using a $^{32}$P-labeled oligonucleotide probe. Squares and circles indicate the results, with transduced cells of the ribozyme 2 (Rz2) and the ribozyme 3 (Rz3), respectively. Panel B indicates the results of Southern blotting. Panel C. Cells were cultured for 11 days after infection with HIV-1 NL432. Small aliquots of supernatant were prepared from each culture on days 3, 7, and 11. Levels of p24 antigen were determined by HIV-1 antigen-capture ELISA. The triangles indicate the result of tRNA$^{Val}$-ribozyme 1 (Rz1). Squares and circles indicate the results with the ribozyme 2 (Rz2) and ribozyme 3 (Rz3), respectively. Triangles indicate the results with the control.

Before the virus-challenge assay, we measured the steady-state level of each tRNA$^{Val}$-ribozyme in the transduced H9 cells by quantitative RT-PCR analysis. The results of the transient expression assay in HeLa cells shown in FIG. 3B, namely, that the difference in steady-state levels of Rz2 and Rz3 was about 5-fold, were confirmed by the RT-PCR analysis (FIGS. 6A and 6B). Clearly, Rz2 was more stable in vivo than Rz3.

When we challenged stable H9 transformants that produced a tRNA$^{Val}$-ribozyme constitutively with HIV-1 virions, Rz2 inhibited viral replication almost completely (about 99%), as determined on day 11 post-infection (FIG. 6C). By contrast, to our surprise, Rz3 failed to inhibit viral replication at all under these experimental conditions. In the HIV-1 challenge assay, the difference between the effects of Rz2 and Rz3 was conspicuous.

Intracellular Localization of the tRNA - ribozymes

Figure 7:
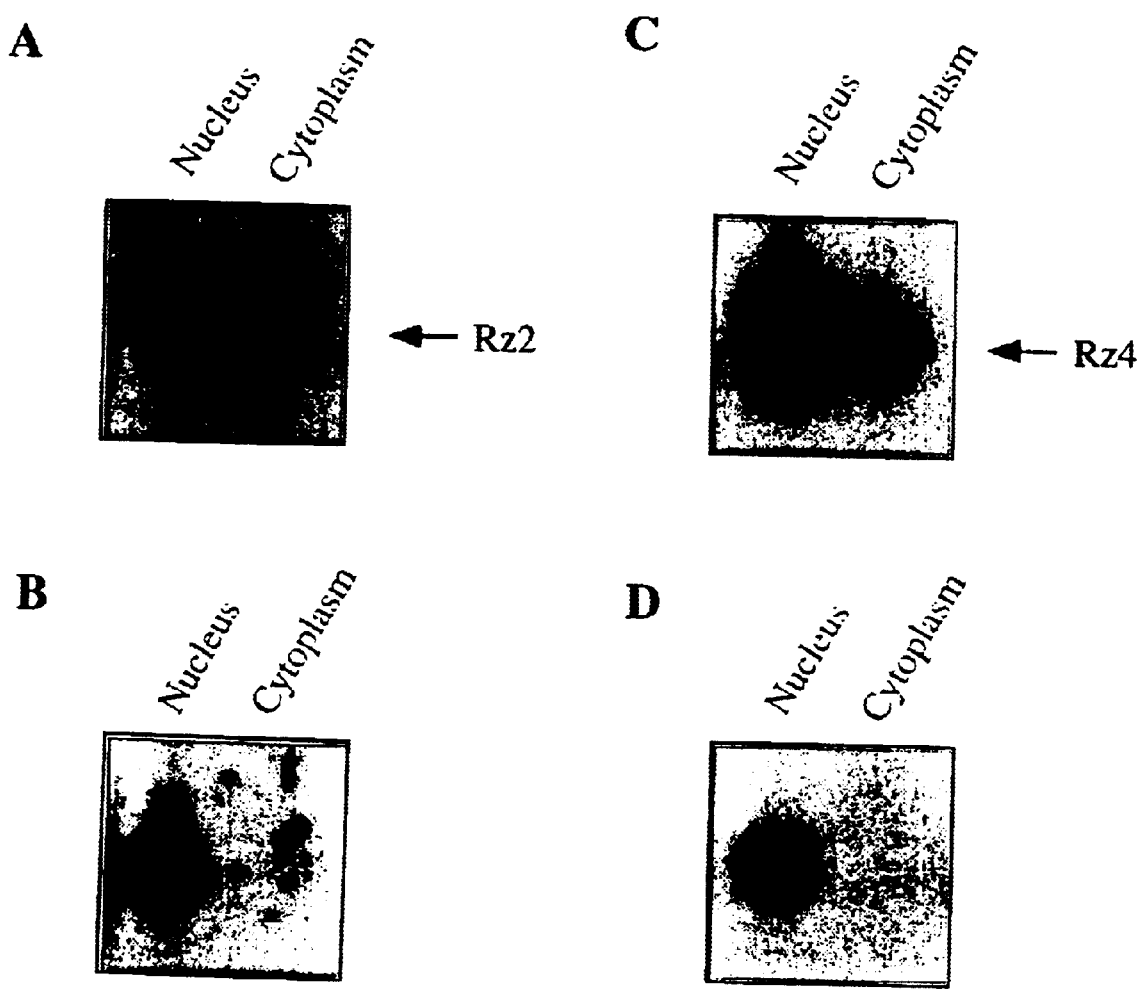
FIGS. 7(A–D) shows intracellular localization of the tRNA$^{Val}$-ribozyme. Northern blotting analysis was performed using RNA from each intracellular fraction. Nucleic and cytoplasmic RNAs were prepared separately from cells that had been stably transduced with the gene for a ribozyme (the tRNA$^{Val}$-ribozyme-producing HeLa cells used in the experiments for which results are given in FIG. 4B). A and C show the results obtained with a $^{32}$P-labeled probe specific for the tRNA$^{Val}$-ribozyme. B and D show controls: Contamination of the cytoplasmic fractions was examined with a probe specific for the transcript of the natural U6 gene.

Since the co-localization of a ribozyme with its target is clearly an important determinant of the ribozyme's efficiency (Sullenger and Cech, 1993; Bertrand et al., 1997), it was essential to determine the intracellular localization of tRNA$^{Val}$-ribozymes. Total RNA from HeLa cells transduced with the Rz2 expression cassette was separated into nuclear and cytoplasmic fractions. Then, transcribed Rz2 was detected by Northern blotting analysis with a probe specifc for the ribozyme. As shown in FIG. 7A, Rz2 was found predominantly in the cytoplasmic fraction and it was not detected to any significant extent in the nuclear fraction. The other tRNA-ribozymes (Rz1 and Rz3) were also localized predominantly in cytoplasmic fractions (data not shown). U6 snRNA, which remains in the nucleus, was included as a control in these studies (FIG. 7B).

Discussion

A ribozyme is a potentially useful tool for the suppression of the expression of specific gene since it can be engineered to act on other RNA molecules with high specificity (Uhlenbeck, 1987; Hasseloff and Gerlach, 1988). Although many trials have been successful (Eckstein and Lilley, 1996; Turner, 1997; Scalon, 1997), it remains difficult to design an effective ribozyme-expression system that can be used in vivo. One major challenge related to the use of ribozymes and antisense RNAs as therapeutics or genetic agents is the development of suitable expression vectors (Jennings and Molloy, 1987; Sullenger et al., 1990; Bertrand et al., 1994, 1997; Thompson et al., 1995). Two kinds of expression system have been used to date, as discussed in the Introduction, namely, the pol II system and pol III system. In this study, we used the pol III system and the promoter of a human gene for tRNA$^{Val}$ for transcription of ribozymes (Yu et al., 1993). This promoter is not only suitable for transcription of small RNAs, but its use also facilitates prediction of secondary structure by computer folding. More importantly, it allows export of transcribed ribozymes from the nucleus to the cytoplasm so that the tRNA$^{Val}$-ribozymes can find with their mRNA targets.

Design of Expression Cassettes

These secondary structure of a target mRNA determines its susceptibility to ribozyme-mediated cleavage, and the ribozyme must also fold into appropriate secondary and tertiary structures for maximal activity. Although there is no guarantee that a computer-predicted secondary structure really represents the corresponding structure after transcription, the structures predicted in this study (FIGS. 1A–1C) were well correlated with cleavage activities In vicro (FIG. 2). In the expression cassettes, the last seven bases of the mature tRNA$^{Val}$(indicated by capital letters in FIG. 1E) had been removed, without any effect on transcription, in order to block 3'-end processing of the transcript (Adeniyi-Jones et al., 1984). They were replaced by a linker (lowercase letters in FIG. 1) followed by a ribozyme (bold capital letters). The freedom or availability of the substrate-recognition arms was adjusted by the linker sequence via formation of stable stem structures in combination with the sequence of the tRNA$^{Val}$ which accounted for about two-thirds of the whole sequence. Thus, it was relatively easy to predict, by computer folding, the secondary structure and the accessibility of each recognition arm. Furthermore, even if the sequence of the substrate recognition arm is changed, as long as the same rules for predicting overall secondary structure are used, it is still possible to predict the accessibility of recognition arms. Indeed, we have succeeded in constructing a similar ribozyme-expression system for inhibition of the expression of other genes (Kawasaki et al., 1996, 1998). Our expression system, as shown in FIGS. 1A–1C, facilitates the design of an effective ribozyme-expression cassette.

Translocation of tRNA$^{Val}$-ribozyme From the Nucleus to the Cytoplasm

The ribozyme-expression cassettes shown in FIGS. 1A–1C allowed all the transcripts to be exported to the cytoplasm (FIG. 7A) where they could find their mRNA targets, and significant inhibition by ribozymes of the expression of the target molecules was observed (FIGS. 4 and 6C). In a previous study (Bertrand et al., 1997), deletion of the last ten bases of mature tRNA$^{Met}$ not only blocked 3' processing but also inhibited the export of the transcript to cytoplasm (Tobian et al., 1985). These results suggested that 3' processing might be linked to export to the cytoplasm and that 3'-altered tRNA transcripts are not exported efficiently (Cotten and Birnstiel, 1989; Boelens et al., 1995). However, as demonstrated in FIG. 7, the deletion of the last seven bases of mature tRNA$^{Val}$ did not inhibit the export of the transcripts from the nucleus.

A protein, designated Exportin(tRNA), which transports tRNA from the nucleus to the cytoplasm has recently been identified (Arts et al., 1998). Exportin (tRNA) binds RanGTP in the absence of tRNA but it does not bind tRNA in the absense of RanGTP. Therefore, a model for the transport of tRNAs was proposed wherein Exportin (tRNA) associates with RanGTP first in the nucleus and then the complex binds a mature tRNA molecule. This final complex is translocated through a nuclear pore complex to the cytoplasm. There, the Ran-bound GTP is hydrolyzed, releasing the tRNA into the cytoplasm and allowing Exportin (tRNA) to be recycled to the nucleus (Arts et al., 1998). We do not yet know the minimal sequence or structure within a tRNA that can be recognized by Exportin (tRNA). However, since the ribozymes shown in FIGS. 1A–1C were successfully translocated to the cytoplasm, it is possible that they were recognized and transported by Exportin (tRNA) despite the deletions and alterations at the 3' end of the natural tRNA.

It is clear, from our study, that even 3'-altered tRNA transcripts can be transported efficiently to the cytoplasm if their secondary structures resemble those in FIGS. 1A–1C. When we tried similarly to express an other kind of ribozyme (Rz4 in FIG. 1D(SEQ ID NO: 5)) in HeLa cells, the transcripts remained in the nucleus (FIG. 7C). The secondary structure of Rz4 (FIG. 1D) is quite different from that of ribozymes Rz1, Rz2 and Rz3, which were cytoplasmic, despite the fact that not only the A and B box promoter elements (shaded boxes in FIG. 1) but also all the remaining sequence within the tRNA$^{Val}$ segment were identical in transcripts Rz1 through Rz4. This observation suggest that, if Exportin (tRNA) can indeed recognize the ribozyme transcript, it is unlikely that it recognizes a specific nucleotide sequence. Exportin (tRNA) might, rather, recognize some specific higher-order structure of tRNA or some sequence within such a higher-order structure.

Indeed, another ribozyme, constructed for other purposes, whose secondary structure resembled that of Rz4 was found only in nuclei (data not shown). We have constructed more than ten other ribozymes for suppression of three other genes, keeping in mind that their secondary structures should resemble those of Rz1 through Rz3 in FIG. 1 and adjusting linker sequences so that they might be transported to the cytoplasm. All of these ribozymes were found in the cytoplasm after transcription. They not only had high activities (>95% inhibition) but also high specificity (<5% inhibition by the inactive control). Thus, cytoplasmic ribozymes based on the design shown in FIGS. 1A–1C seem very attractive (Kawasaki et al., 1996, 1998). We should also mention that the secondary structures of Rossi's tRNA$^{Met}$-ribozymes, which remained in nuclei and were not very active (Bertrand et al., 1997), do not resemble our active secondary structures because of their different linker sequence. Their structures resemble that of Rz4 (computer-predicted structures not shown).

It will be of interest to determine whether ribozymes such as Rz1 through Rz3 (but not Rz4 or Rossi's tRNA$^{Met}$-ribozymes) form complexes with Exportin (tRNA) in the presence of RanGTP, that is, under conditions in which formation of a complex between an export receptor and its cargo would be expected (Arts et al., 1998).

Activities of tRNA$^{Val}$-ribozyme in vivo

Sullenger and Cech (1993) and Rossi's group (Bertrand et al., 1997) clearly demonstrated the importance of intracellular co-localization of ribozymes with their targets. In the case of one specific expression cassette, both the ribozymes and its RNA target were located in the nucleus and the specific cleavage by the ribozyme of its target was detected (Bertrand et al., 1994). Thus, the critical parameter is not the localization of the ribozyme per se but it is, rather, the ability of the ribozyme to co-localize with its target (Bertrand et al., 1997). Since various proteinaceous factors are involved in the intracellular processing and transport of mRNAs and since such factors may bind promptly with mRNA immediately after transcription, such factors could inhibit the binding of the ribozyme with its RNA target in the nucleus. Also, in the cytoplasm, polysomes might inhibit the binding of the ribozyme with its RNA target. Moreover, since nuclear tRNA$^{Met}$-ribozyme failed to inactivate a cytoplasmic mRNA that had originally been produced in the nucleus (Bertrand et al., 1997), the transport of mRNA from the nucleus to the cytoplasm seems to be much more rapid than the attack by the nuclear tRNA$^{Met}$-ribozyme. One of the most critical factors determining ribozyme activity in vivo seems to be the association between the ribozyme and its target. A significant fraction of ribozymes must be degraded during their transport and also during their approach to their target site. For this reason, co-localization of a ribozyme and its target does not, by itself, guarantee the efficacy of ribozymes in vivo.

The ribozyme Rz2, which was most stable in vivo (FIGS. 3B, 3C, 6A and 6B), was more effective in the intracellular environment (FIG. 4) than Rz3, which had higher cleavage activity in vitro (FIG. 2). This difference in activity was magnified in the HIV-1 challenge (FIG. 6C). Although cells producing the more stable Rz2 were almost completely resistant to infection by HIV-1, other cells producing the less stable Rz3 were as sensitive as control cells to infection by HIV-1. Although Rz2 had a half-life, that was about twice that of Rz3, it is unclear, at present, which structural feature(s) made Rz2 more resistant to RNases. There were six more nucleotides within the linker in Rz3, as compared to Rz2, which must have influenced the higher-order structure.

The half-lives of natural tRNAs range from 50 to 60 hours (Smith and Weinberg, 1981), while that of Rz2 was only about 100 min. If the half-life of the tRNA-ribozyme could be prolonged, a higher inhibitory effect might be expected. While we still cannot predict the relative stabilities of transcripts in vivo, we can design ribozymes that can be transported into the cytoplasm by incorporating secondary structures such as the ones shown in FIG. 1. Since we cannot accurately predict the stability of a transcript, we usually test several constructs and, in the case of various genes tested to date, we have always been able to obtain a cassette that can inactivate the gene of interest with >95% efficiency (Kawasaki et al., 1996, 1998)

The tRNA$^{Val}$-vector may be useful for expression of functional RNAs other than ribozymes whose target molecules are localized in the cytoplasm. In our hands, tRNA$^{Val}$-ribozymes have consistently high activities, at least in cultured cells. Therefore, properly designed tRNA$^{Val}$-ribozymes appeared to be very useful as tools in molecular biology, with potential utility in medicine as well.

INDUSTRIAL APPLICABILITY

By the present invention, there is provided novel ribozymes and expression systems therefor. The ribozyme of the present invention has high in vivo stability, and thereby exhibits high activity.

References

Adachi, A. Gendelman, H. E., Koenig, S., Folks, T., Willey, R., Rabson, A. and Martin, M. A. (1986) Production of acquired immunodeficiency syndrome-associated retrovirus in human and nonhuman cells transfected with an infectious molecular clone. J. Virol., 59, 284–291.

Adeniyi-Jones, S., Romeo, P. and Zasloff, M. (1984) Generation of long read through transcripts in vivo and in vitro by deletion of 3' termination and processing sequences in the human tRNAi met gene. Nucleic Acids Res., 12, 1101–1115.

Arnold, G. J., Schmutzler, C., Thomann, U., van Tol, H. and Gross, H. J. (1986) The human tRNA$^{Val}$ gene family: organization, nucleotide sequences and homologous transcription of three single-copy genes. Gene, 44, 287–297.

Arts, G.-J., Fornerod, M. and Mattaj, I. W. (1998) Identification of a nuclear export receptor for tRNA. Curr. Biol., 6, 305–314.

Bertrand, E., Pictet, R. and Grange, T. (1994) Can hammerhead ribozymes be efficient tools for inactivating gene function? Nucleic Acids Res., 22, 293–300.

Bertrand, E. and Rossi, J. J. (1996) Anti-HIV therapeutic hammerhead ribozymes: targeting strategies and optimization of intracellular function. In Eckstein, F. and Lilley, D. M. J. (eds.) Nucleic Acids Mol. Biol., Vol.10. Springer-verlag, Berlin, 301–313.

Bertrand, E. Castanotto, D., Zhou, C., Carbonnelle, C., Lee. G. P., Chatterjee, S., Grange, T., Pictet, R., Kohn, D., Engelke, D. and Rossi, J. J. (1997) The expression cassette determines the functional activity of ribozymes in mammalian cells by controlling their intracellular localization. RNA, 3, 75–88.

Boelens, W., Palacios, I. and Mattaj, I. W. (1995) Nuclear retention of RNA as a mechanism for localization. RNA, 1, 273–283.

Cotten, M. and Birnstiel, M. (1989) Ribozyme mediated destruction of RNA in vivo. EMBO J., 8, 3861–3866.

Dahm, S. C. and Uhlenbeck, O. C. (1991) Role of divalent metal ions in the hammerhead RNA cleavage reaction. Biochemistry, 30, 9464–9469.

Dahm, S. C., Derrick, W. B. and Uhlenbeck, O. C. (1993) Evidence for the role of solvated metal hydroxide in the hammerhead cleavage mechanism. Biochemistry, 32, 13040–13045.

Dropulic, B., Lin, N. H., Martin, M. A. and Jeang, K. T. (1992) Functional characterization of a U5 ribozyme: intracellular suppression of human immunodeficiency virus type 1 expression. J. Virol., 66, 1432–1441.

Eckstein, F. and Lilley, D. M. J. (eds.) (1996) Catalytic RNA, Nucleic Acids and Molecular Biology, Vol.10. Springer-Verlag, Berlin.

Erickson, R. P. and Izant, J. (eds.) (1992) Gene Reguration: Biology of Antisense RNA and DNA; Raven Perss, New York.

Ferbeyre, G., Bratty, J., Chen, H. and Cedergren, R. (1996) Cell cycle arrest trans-hammerhead ribozyme action in Yeast. J. Biol. Chem., 271, 19318–19323.

Fujita, S., Koguma, T., Ohkawa, J., Mori, K., Kohda, T., Kise, H., Nishikawa, S., Iwakura, M. K. and Taira. K. (1997) Discrimination of a single base change in a ribozyme using the gene for dihydrofolate reductase as a selective marker in Escherichia coli. Proc. Natl. Acad. Sci. USA, 94, 391–396.

Gebhard. J. R., Perry, C. M., Mahadeviah, S. and Witton, J. L. (1997) Use of a nonviral vector to express a chimeric tRNA-ribozyme against lymphocytic choriomeningitis virus: cytoplasmic accumulation of a catalytically competent transcript but minimal antiviral effect. Antisense and Nucleic Acid Drug Dev. 7, 3–11.

Good. P. D., Krikos, A. J., Li, S. X. L., Lee, N. S., Giver, L., Ellington, A., Zaia, J. A., Rossi, J. J. and Engelke, D. R. (1997) Expression of small, therapeutic RNAs in human cell nuclei. Gene Therapy, 4, 45–54.

Guerrier-Takada, C., Gardiner, K., Marsh, T., Pace, N. and Altman, S. (1983) The RNA moiety of ribonuclease P is the catalytic subunit of the enzyme. Cell, 35, 849–857.

Hamblet, N. S. and Castora, F. J. (1995) Mitochondrial DNA deletion analysis: a comparison of PCR quantitative methods. Biochem. Biophys. Res. Commun., 207, 839–847.

Hasseloff, J. and Gerlach, W. L. (1988) Simple RNA enzymes with new and highly specific endoribonuclease activities. Nature, 334, 585–591.

Huang, Y. and Carmichael, G. G. (1996) Role of polyadenylation in nucleocytoplasmic transport of mRNA. Mol. Cell. Biol., 16, 1534–1542.

Inokuchi, Y., Yuyama, N., Hirashima. A., Nishikawa, S., Ohkawa, J., and Taira, K. (1994) A hammerhead ribozyme inhibits the proliferation of an RNA coliphage SP in E. coli. J. Biol. Chem., 269, 11361–11366.

Ilves, H., Barske, C., Junker, U., Bohnlein, E. and Veres, G. (1996) Retroviral vectors designed for targeted expression of RNA polymerase III-driven transcripts: a comparative study. Gene, 171, 203–208.

Jennings, P. A. and Molloy, P. L. (1987) Inhibition of SV40 replicon function by engineered anitisense RNA tranncribed by RNA polymerase III. EMBO 3, 6, 3043–3047.

Kawasaki, H., Ohkawa, J., Tanishige, N., Yoshinari, K., Murata, T., Yokoyama, K. K. and Taira, K. (1996) Selection of the best target site for ribozyme-mediated cleavage within a fusion gene for adenovirus ElA-associated 300 kDa protein (p300) and luciferase. Nucleic Acids Res. 24, 3010–3016.

Kawasaki, H., Ecker, R., Yao, T.-P., Taira, K., Chiu, R., Livingston, D. M. and Yokoyama, K. K. (1998) Distinct roles of the co-activators p300 and CBP in retinoic-acid-induced F9-cell differentiation Nature, 393, 284–289.

Kruger, K., Grabowski, P. J., Zaug, A. J., Sands, J., Gottschling. D. E. and Cech, T. R. (1982) Self-splicing RNA: autoexcision and autocyclization of the ribosomal RNA intervening sequence of Tetrahymena. Cell, 31, 147–157.

Lott, W. B., Pontius, B. W. and von Hippel, P. H. (1998) A two-metal ion mechanism operates in the hammerhead ribozyme-mediated cleavage of an RNA substrate, Proc Natl. Acad. Sci. USA, 95, 542–547.

Murray, J. A. H. (ed.)(1992) Antisense RNA and DNA; Wiley-Liss, Inc, New York.

Ohkawa, J., Yuyama, N., Takebe, Y., Nishikawa, S. and Taira, K. (1993) Importance of independence in ribozyme reactions: kinetic behavior of trimmed and of simply connected multiple ribozymes with potential activity against human immunodeficiency virus. Proc. Natl. Acad. Sci. USA, 90, 11302–11306.

Ojwang, J. O.,Hampel, A., Looney, D. J., Wong-Staal, F. and Rappaport, J. (1992) Inhibition of human immunodeficiency virus type 1 expression by a hairpin ribozyme. Proc. Natl. Acad. Sci. USA, 89, 10802–10806.

Ozawa, T., Tanaka, M., Ikebe, S., Ohno, K., Kondo, T. and Mizuno, Y, (1990) Quantitative determination of deleted mitochondrial DNA relative to normal DNA in parkinsonian striatum by a kinetic PCR analysis. Biochem. Biophys. Res. Commun., 172, 483–489.

Perriman, R., Bruening, G., Dennis E. S. and Peacock, W. J. (1995) Effective ribozyme delivery in plant cells. Proc. Natl. Acad. Sci. USA, 92, 6175–6179.

Pontius, B. W., Lott, W. B. and von Hippel, P. H. (1997) Observations on catalysis by hammerhead ribozymes are consistent with a two-divalent-metal-ion mechanism. Proc. Natl. Acad. Sci. USA, 94, 2290–2294.

Prislei, S., Buonomo, S. B. C., Michienzi, A. and Bozzoni I. (1997) Use of adenoviral VAI small RNA as a carrier for cytoplasmic delivery of ribozymes. RNA, 3, 677–687.

Rossi, J. J. and Sarver, N. (1990) RNA enzymes (ribozymes) as antiviral therapeutic agnts. TIBTECH, 8, 179–183.

Rossi, J. J. (1995) Controlled, targeted, intracellular expression of ribozymes: progress and problems. TIBTECH, 13, 301–306.

Sarver, N., Cantin, E. M., Chang, P. S., Zaida, J. A., Ladne, P. A., Stepenes, D. A. and Rossi, J. J. (1990) Ribozymes as potential anti-HIV-1 therapeutic agents. Science, 247, 1222–1225.

Scanlon, K. J. (ed.) (1997) Therapeutic Applications of Ribozymes; Methods, in Molecular Medicine, Vol.11, Humana Press, New Jersey.

Shimada, T., Fujii, H., Mitsuya, H. and Nienhuis, A. W. (1991) Targeted and highly efficient gene transfer into CD4+cells by a recombinant human immunodeficiency virus retroviral vector. J. Clin. Invest.,88, 1043–1047.

Smith, D. W. and Weinberg, W. C. (1981) Transfer RNA in reticulocyte maturation. Biochem. Biophys. Acta., 655, 195–198.

Sullenger, B. A., Lee, T. C., Smith, C. A. and Ungers, G. E. (1990) Expression of chimeric tRNA-driven antisense transcripts renders NIH 3T3 cells highly resistant to Moloney murine leukemia virus replication. Mol. Cell. Biol. 10, 6512–6523.

Sullenger, B. A. and Cech, T. R. (1993) Tethering ribozymes to a retroviral packaging signal for destruction of viral RNA. Science, 262, 1566–1569.

Taira, K., Nakagawa, K., Nishikawa, S. and Furukawa, K. (1991) Construction of a novel RNA-transcript-trimming plasmid which can be used both in vitro in place of run-off and (G)-free transcriptions and in vivo ad multi-sequence transcription vectors. Nucleic Acids Res., 19, 5152–5130.

Thomas, K. R. and Capecchi, H. R. (1987) Site-directed mutagenesis by gene targeting in mouse embryo-derived stem cells. Cell, 51, 503–512.

Thompson, D. J., Ayers, F. D., Malmstrom. A. T., Ganousis, L. M., Chowrira, M. B., Couture. L. and Stinchcomb, T. D. (1995) Improved accumulation and activity of ribozymes expressed from a tRNA-based RNA polymerase III promoter. Nucleic Acids Res., 23, 2259–2268.

Tobian, J. A., Drinkard, L. and Zaseloff, M. (1985) tRNA nuclear transport: defining the critical regions of human tRNA Met by point mutagenesis. Cell, 43, 415–422.

Turner, P. C. (ed.) (1997) Ribozyme Protocols; Methods in Molecular Biology. Vol.74, Humana Press. New Jersey.

Uhlenbeck, O. C. (1987) A small catalytic oligoribonucleotide. Nature, 328,596–600.

Yamada, O., Kraus, G. Leavitt, M. C., Yu, M. and Wong-Staal, F. (1994) Activity and cleavage site specificity of an anti-HIV-1 hairpin ribozyme in human T cells. Virology, 205, 121–126.

Yamada, O., Yu, M., Yee, J.-K., Kraus, G., Looney, D. and Wong-Staal, F. (1994) Intracellular immunization of human T cells with a hairpin ribozyme against human immunodeficiency virus type 1. Gene Therapy, 1, 38–45.

Yates, J. Warren, N., Reisman, D. and Sugden, B. (1984) A cis-acting element from the Epstein-Barr viral genome that permits stable replication of recombinant plasmids in latently infected cells. Proc. Natl. Acad. Sci. USA, 81, 3806–3810.

Yu, M., Ojwang, J. O., Yamada, O., Hampel, A., Rappaport, J., Looney, D. and Wong-Staal, F. (1993) A hairpin ribozyme inhibits expression of diverse strains of human immunodeficiency virus type 1. Proc. Natl. Acad. Sci. USA, 90, 6340–6344.

Zhao, J. J. and Pick, K, (1993) Generating loss-of function phenotypes of the fushitarazu gene with a targeted ribozyme in Drosophila. Nature, 365. 448–451.

Zhou, D.-M., Zhang, L.-H. Kumar, P. K. R. and Taira, K. (1996) The ribozyme mechanism revisited: Evidence against direst coordination of a $Mg^{2+}$ ion with the pro-R oxygen of the scissile phosphate in the transition state of a hammerhead ribozyme-catalyzed reaction. J. Am. Chem. Soc., 118, 8969–8970.

Zhou, D.-M., Zhang, L.-H. and Taira, K. (1997) Explanation by the double-metal-ion mechanism of catalysis for the differential metal ion effects on the cleavage rates of 5'-oxy and 5'-thio substrates by a hammerhead ribozyme. Proc. Natl. Acad. Sci. USA, 94, 14343–14348.

Zhou, D.-M. and Taira. K. (1998) The hydrolysis of RNA: from theoretical calculations to the hammerhead ribozyme-mediated cleavage of RNA. Chem. Rev, 98, 991–1026.

All documents, patent applications and patents referred to herein are incorporated in their entirety into the present specification.

What is claimed is:

1. A ribozyme comprising a nucleotide sequence having the following base sequence (I) or (II):
   base sequence (I)(SEQ ID No. 1): 5'-ACCGUUGGUUUCCGUAGUGUAGUGGUUAUCACGUUCGCCUAACACGCGAAAGGUC-CCCGGUUCGAAACCGGGCACUACAAACACAACACUGAUGAGGACCGAAAGGUC-CGAAACGGGCACGUCGGAAAACGGUUUU[[U]]-3'
   base sequence (II)(SEQ ID No. 2): 5'-ACCGUUGGUUUCCGUAGUGUAGUGGUUAUCACGUUCGCCUAACACGCGAAAGGUC-CCCGGUUCGAACCGGGCACUACAAA CCAA-CACACAACACUGAUGAGGACCGAAAG-GUCCGAAACGGGCACGUCGGAAAC GGUUUU[[U]]-3'.

2. An expression vector comprising DNA encoding the ribozyme according to claim 1.

3. A method of producing the ribozyme according to claim 1 comprising transcribing to RNA with expression vector DNA as a template, wherein said expression vector DNA comprises DNA encoding the ribozyme according to claim 1.

4. A composition comprising the ribozyme according to claim 1 or the expression vector according to claim 2.

5. A method of specifically cleaving a target RNA using the ribozyme according to claim 1, comprising administering the ribozyme to one or more isolated cells.

6. The method of claim 5 wherein the target RNA is HIV-1 RNA.

7. An RNA variant consisting of the sequence of a region corresponding to nucleotides 1–80 within the nucleotide sequence represented by SEQ ID NO: 1.

8. An RNA variant consisting of the sequence of a region corresponding to nucleotides 1–86 within the nucleotide sequence represented by SEQ ID NO: 2.

9. A method of specifically cleaving a target RNA in vitro using the ribozyme according to claim 1.

* * * * *

SEQUENCE LISTING

<160> NUMBER OF SEQ ID NOS: 25

<210> SEQ ID NO 1
<211> LENGTH: 135
<212> TYPE: RNA
<213> ORGANISM: Artificial Sequence
<220> FEATURE:
<223> OTHER INFORMATION: Description of Artificial Sequence: Nucleotide
      sequence of Rz2

<400> SEQUENCE: 1
accguugguu uccguagugu agugguuauc acguucgccu aacacgcgaa aggucccgg      60 uucgaaaccg ggcacuacaa acacaacacu gaugaggacc gaaaggaccg aaacgggcac    120
gucggaaacg guuuu                                                     135

<210> SEQ ID NO 2
<211> LENGTH: 141
<212> TYPE: RNA
<213> ORGANISM: Artificial Sequence
<220> FEATURE:
<223> OTHER INFORMATION: Description of Artificial Sequence: Nucleotide
      sequence of Rz3

<400> SEQUENCE: 2
accguugguu uccguagugu agugguuauc acguucgccu aacacgcgaa aggucccgg      60 uucgaaaccg ggcacuacaa accaacacac aacacugaug aggaccgaaa gguccgaaac   120
gggcacgucg gaaacgguuu u                                              141

<210> SEQ ID NO 3
<211> LENGTH: 128
<212> TYPE: RNA
<213> ORGANISM: Artificial Sequence
<220> FEATURE:
<223> OTHER INFORMATION: Description of Artificial Sequence: Nucleotide
      sequence of Rz1

<400> SEQUENCE: 3
accguugguu uccguagugu agugguuauc acguucgccu aacacgcgaa aggucccgg      60 uucgaaaccg ggcacccaca caacacugau gaguccguga ggacgaaacg ggcaccucga    120
gcgcuuuu                                                             128

<210> SEQ ID NO 4
<211> LENGTH: 95
<212> TYPE: RNA
<213> ORGANISM: Artificial Sequence
<220> FEATURE:
<223> OTHER INFORMATION: Description of Artificial Sequence: Nucleotide
      sequence of the transcript of human placental tRNA Val

<400> SEQUENCE: 4
accguugguu uccguagugu agugguuauc acguucgccu aacacgcgaa aggucccgg      60 uucgaaaccg ggcggaaaca aagacagucg cuuuu                                95

SEQ ID NO 5
LENGTH: 149
TYPE: RNA
ORGANISM: Artificial Sequence
FEATURE:
OTHER INFORMATION: Description of Artificial Sequence: Nucleotide
sequence of Rz4

-continued

```
SEQUENCE: 5 accguugguu ucgguagugu agugguuauc acguucgccu aacacgcgaa aggucccccg      60
uucgaaaccg ggcacccggg uggcugucac cggaagugcu uuccggucuc augaguccgu     120
gagggcgaaa cagccacucg agcgcuuuu                                       149

<210> SEQ ID NO 6
<211> LENGTH: 110
<212> TYPE: DNA
<213> ORGANISM: Artificial Sequence
<220> FEATURE:
<223> OTHER INFORMATION: Description of Artificial Sequence: Sequence of
      a sense oligonucleotide linker

<400> SEQUENCE: 6
aattcaggac tagtctttta ggtcaaaaag aagaagcttt gtaaccgttg gtttccgtag      60
tgtagtggtt atcacgttcg cctaacacgc gaaaggtccc cggttcgaag               110

<210> SEQ ID NO 7
<211> LENGTH: 113
<212> TYPE: DNA
<213> ORGANISM: Artificial Sequence
<220> FEATURE:
<223> OTHER INFORMATION: Description of Artificial Sequence: Sequence of
      an antisense oligonucleotide linker

<400> SEQUENCE: 7
tcgacttcga accggggacc tttcgcgtgt taggcgaacg tgataaccac tacactacgg      60
aaaccaacgg ttacaaagct tcttcttctt tttgacctaa aagactagtc ctg            113

<210> SEQ ID NO 8
<211> LENGTH: 53
<212> TYPE: DNA
<213> ORGANISM: Artificial Sequence
<220> FEATURE:
<223> OTHER INFORMATION: Description of Artificial Sequence: Sequence of
      a sense oligonucleotide linker

<400> SEQUENCE: 8
cgaaaccggg cacccgggga atataacctc gagcgctttt tttctatcgc gtc            53

<210> SEQ ID NO 9
<211> LENGTH: 54
<212> TYPE: DNA
<213> ORGANISM: Artificial Sequence
<220> FEATURE:
<223> OTHER INFORMATION: Description of Artificial Sequence: Sequence of
      an antisense oligonucleotide linker

<400> SEQUENCE: 9
tcgacgcgat agaaaaaaag cgctcgaggt tatattcccc gggtgcccgg tttc           54

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Sequence of
      an upper primer

<400> SEQUENCE: 10
cgccagggtt tcccagtcac gac                                             23

<210> SEQ ID NO 11
```

```
<211> LENGTH: 101
<212> TYPE: DNA
<213> ORGANISM: Artificial Sequence
<220> FEATURE:
<223> OTHER INFORMATION: Description of Artificial Sequence: Sequence of
      a lower primer including the sequences of Rz1 and a terminator

<400> SEQUENCE: 11
ctgcaggtcg acgcgataga aaaaaagcgc tcgaggtgcc cgtttcgtcc tcacggactc        60
atcagtgttg tgtgggtgcc cggtttcgaa ccgggacctt t                           101

<210> SEQ ID NO 12
<211> LENGTH: 109
<212> TYPE: DNA
<213> ORGANISM: Artificial Sequence
<220> FEATURE:
<223> OTHER INFORMATION: Description of Artificial Sequence: Sequence of
      a lower primer including the sequences of Rz2 and a terminator

<400> SEQUENCE: 12
ctgcaggtcg acgcgataga aaaaaaccgt ttccgacgtg cccgtttcgg tcctttcggt        60
cctcatcagt gttgtgtttg tagtgcccgg tttcgaaccg ggaccttt                    109

<210> SEQ ID NO 13
<211> LENGTH: 106
<212> TYPE: DNA
<213> ORGANISM: Artificial Sequence
<220> FEATURE:
<223> OTHER INFORMATION: Description of Artificial Sequence: Sequence of
      a lower primer including the sequences of Rz3 and a terminator

<400> SEQUENCE: 13
ctgcaggtcg acgcgataga aaaaaccgt ttccgacgtg cccgtttcgg tcctcatcag         60
tgttgtgtgt tggtttgtag tgcccggttt cgaaccgggg accttt                      106

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: Sequence of
      a probe specific for the reference RNA

<400> SEQUENCE: 14
aaatcgctat aaaaagcgct cgaggttatg ctccccgggt                              40

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Sequence of
      a probe specific for the ribozyme

<400> SEQUENCE: 15
ctcatctgtg ttgtgt                                                        16

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Sequence of
      a primer for b-actin

<400> SEQUENCE: 16
```

```
gtggccatct cttgctcgaa                                                    20

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Sequence of
      a primer for the ribozyme

<400> SEQUENCE: 17
gacctttcgg tcctcatc                                                      18

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Sequence of
      an upper oligonucleotide primer

<400> SEQUENCE: 18
gactacctca tgaagatcct                                                    20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Sequence of
      a lower oligonucleotide primer

<400> SEQUENCE: 19
gtggccatct cttgctcgaa                                                    20

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Sequence of
      an upper oligonucleotide primer

<400> SEQUENCE: 20
gttatcacgt tcgcctaa                                                      18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Sequence of
      a lower oligonucleotide primer

<400> SEQUENCE: 21
gacctttcgg tcctcatc                                                      18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Sequence of
      a probe specific for the ribozyme

<400> SEQUENCE: 22
```

```
                                    -continued acgcgaaagg tccccggt                                                         18

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Sequence of
      a probe specific for b-actin

<400> SEQUENCE: 23
gcgggaaaat cgtgcgtga                                                        19

<210> SEQ ID NO 24
<211> LENGTH: 38
<212> TYPE: RNA
<213> ORGANISM: Artificial Sequence
<220> FEATURE:
<223> OTHER INFORMATION: Description of Artificial Sequence: Substrate
      RNA corresponds to nucleotides 500-711 of pNL 432, namely the U5
      region of HIV-1 RNA

<400> SEQUENCE: 24
acacaacacu gaugaguccg ugaggacgaa acgggcac                                   38

<210> SEQ ID NO 25
<211> LENGTH: 17
<212> TYPE: RNA
<213> ORGANISM: Artificial Sequence
<220> FEATURE:
<223> OTHER INFORMATION: Description of Artificial Sequence: Substrate
      RNA corresponds to nucleotides 500-711 of pNL 432, namely the U5
      region of HIV-1 RNA

<400> SEQUENCE: 25
gugcccgucu guugugu                                                          17
```